US012156724B2

(12) United States Patent
Addison et al.

(10) Patent No.: US 12,156,724 B2
(45) Date of Patent: *Dec. 3, 2024

(54) SYSTEMS AND METHODS FOR VIDEO-BASED PATIENT MONITORING DURING SURGERY

(71) Applicant: Covidien LP, Mansfield, MA (US)

(72) Inventors: Paul Stanley Addison, Edinburgh (GB); David Ming Hui Foo, Glasgow (GB); Dominique Jacquel, Edinburgh (GB)

(73) Assignee: Covidien LP, Mansfield, MA (US)

( * ) Notice: Subject to any disclaimer, the term of this patent is extended or adjusted under 35 U.S.C. 154(b) by 117 days.

This patent is subject to a terminal disclaimer.

(21) Appl. No.: 18/053,337

(22) Filed: Nov. 7, 2022

(65) Prior Publication Data

US 2023/0110666 A1 Apr. 13, 2023

Related U.S. Application Data

(63) Continuation of application No. 16/431,384, filed on Jun. 4, 2019, now Pat. No. 11,510,584.

(Continued)

(51) Int. Cl.
*A61B 5/00* (2006.01)
*A61B 5/024* (2006.01)
(Continued)

(52) U.S. Cl.
CPC .......... *A61B 5/0261* (2013.01); *A61B 5/0037* (2013.01); *A61B 5/02444* (2013.01);
(Continued)

(58) Field of Classification Search
CPC . A61B 5/0261; A61B 5/0037; A61B 5/02444; A61B 5/7425; A61B 34/20;
(Continued)

(56) References Cited

U.S. PATENT DOCUMENTS

| 5,107,845 A | 4/1992 | Guern et al. |
| 5,408,998 A | 4/1995 | Mersch |

(Continued)

FOREIGN PATENT DOCUMENTS

| CA | 2234191 A1 | 10/1998 |
| CN | 106725410 A | 5/2017 |

(Continued)

OTHER PUBLICATIONS

Kwon, Sungjun, et al., "Validation of heart rate extraction using video imaging on a built-in camera system of a smartphone", 34th Annual International Conference of the IEEE EMBS, San Diego, CA, USA, Aug. 28-Sep. 1, 2012, pp. 2174-2177, 4 pages.

(Continued)

*Primary Examiner* — Joel Lamprecht
(74) *Attorney, Agent, or Firm* — Draft Masters IP, LLC

(57) ABSTRACT

The present invention relates to the field of medical monitoring, and in particular non-contact monitoring of one or more physiological parameters in a region of a patient during surgery. Systems, methods, and computer readable media are described for generating a pulsation field and/or a pulsation strength field of a region of interest (ROI) in a patient across a field of view of an image capture device, such as a video camera. The pulsation field and/or the pulsation strength field can be generated from changes in light intensities and/or colors of pixels in a video sequence captured by the image capture device. The pulsation field and/or the pulsation strength field can be combined with indocyanine green (ICG) information regarding ICG dye injected into the patient to identify sites where blood flow has decreased and/or ceased and that are at risk of hypoxia.

15 Claims, 12 Drawing Sheets

Related U.S. Application Data

(60) Provisional application No. 62/695,244, filed on Jul. 9, 2018, provisional application No. 62/685,485, filed on Jun. 15, 2018.

(51) Int. Cl.
| | |
|---|---|
| *A61B 5/026* | (2006.01) |
| *A61B 34/20* | (2016.01) |
| *A61B 90/00* | (2016.01) |
| *G06T 7/00* | (2017.01) |
| *G16H 30/00* | (2018.01) |
| *G16H 40/60* | (2018.01) |
| *G16H 40/63* | (2018.01) |

(52) U.S. Cl.
CPC .......... *A61B 5/7425* (2013.01); *A61B 34/20* (2016.02); *A61B 90/361* (2016.02); *A61B 90/37* (2016.02); *A61B 90/39* (2016.02); *G06T 7/0012* (2013.01); *G16H 30/00* (2018.01); *G16H 40/60* (2018.01); *G16H 40/63* (2018.01); *A61B 2034/2055* (2016.02); *A61B 2090/371* (2016.02); *A61B 2090/373* (2016.02); *A61B 2090/3983* (2016.02); *G06T 2207/30004* (2013.01); *G06T 2207/30048* (2013.01); *G06T 2207/30061* (2013.01); *G06T 2207/30101* (2013.01); *G06T 2207/30104* (2013.01)

(58) Field of Classification Search
CPC ....... A61B 90/361; A61B 90/37; A61B 90/39; A61B 2034/2055; A61B 2090/371; A61B 2090/373; A61B 2090/3983; A61B 5/746; A61B 2505/05; A61B 5/14542; A61B 5/0295; A61B 5/1032; A61B 5/743; A61B 5/02416; A61B 5/0275; G06T 7/0012; G06T 2207/30004; G06T 2207/30048; G06T 2207/30061; G06T 2207/30101; G06T 2207/30104; G16H 30/00; G16H 40/60; G16H 40/63

See application file for complete search history.

(56) References Cited

U.S. PATENT DOCUMENTS

| | | | |
|---|---|---|---|
| 5,704,367 | A | 1/1998 | Ishikawa et al. |
| 5,800,360 | A | 9/1998 | Kisner et al. |
| 5,995,856 | A | 11/1999 | Mannheimer et al. |
| 6,241,684 | B1 | 6/2001 | Amano et al. |
| 6,668,071 | B1 | 12/2003 | Minkin et al. |
| 6,920,236 | B2 | 7/2005 | Prokoski |
| 7,431,700 | B2 | 10/2008 | Aoki et al. |
| 7,558,618 | B1 | 7/2009 | Williams |
| 8,149,273 | B2 | 4/2012 | Liu et al. |
| 8,754,772 | B2 | 6/2014 | Horng et al. |
| 8,792,969 | B2 | 7/2014 | Bernal et al. |
| 8,971,985 | B2 | 3/2015 | Bernal et al. |
| 9,226,691 | B2 | 1/2016 | Bernal et al. |
| 9,282,725 | B2 | 3/2016 | Jensen-Jarolim et al. |
| 9,301,710 | B2 | 4/2016 | Mestha et al. |
| 9,402,601 | B1 | 8/2016 | Berger et al. |
| 9,436,984 | B2 | 9/2016 | Xu et al. |
| 9,443,289 | B2 | 9/2016 | Xu et al. |
| 9,504,426 | B2 | 11/2016 | Kyal et al. |
| 9,508,141 | B2 | 11/2016 | Khachaturian et al. |
| 9,607,138 | B1 | 3/2017 | Baldwin et al. |
| 9,662,022 | B2 | 5/2017 | Kyal et al. |
| 9,693,693 | B2 | 7/2017 | Farag et al. |
| 9,693,710 | B2 | 7/2017 | Mestha et al. |
| 9,697,599 | B2 | 7/2017 | Prasad et al. |
| 9,750,461 | B1 | 9/2017 | Telfort |
| 9,839,756 | B2 | 12/2017 | Klasek |
| 9,943,371 | B2 | 4/2018 | Bresch et al. |
| 10,213,540 | B2 | 2/2019 | Burbank et al. |
| 10,278,585 | B2 | 5/2019 | Ferguson et al. |
| 10,376,147 | B2 | 8/2019 | Wood et al. |
| 10,398,353 | B2 | 9/2019 | Addison et al. |
| 10,447,972 | B2 | 10/2019 | Patil |
| 10,489,912 | B1 | 11/2019 | Brailovskiy |
| 10,523,852 | B2 | 12/2019 | Tzvieli et al. |
| 10,588,779 | B2 | 3/2020 | Vorhees et al. |
| 10,589,916 | B2 | 3/2020 | McRae |
| 10,650,585 | B2 | 5/2020 | Kiely |
| 10,667,723 | B2 | 6/2020 | Jacquel et al. |
| 10,702,188 | B2 | 7/2020 | Addison et al. |
| 10,729,357 | B2 | 8/2020 | Larson et al. |
| 10,874,331 | B2 | 12/2020 | Kaiser et al. |
| 10,937,296 | B1 | 3/2021 | Kukreja et al. |
| 10,939,824 | B2 | 3/2021 | Addison et al. |
| 10,939,834 | B2 | 3/2021 | Khwaja et al. |
| 10,966,059 | B1 | 3/2021 | Dayal et al. |
| 11,311,252 | B2 | 4/2022 | Jacquel et al. |
| 11,315,275 | B2 | 4/2022 | Addison et al. |
| 11,317,828 | B2 | 5/2022 | Addison et al. |
| 11,350,850 | B2 | 6/2022 | Jacquel et al. |
| 11,510,584 | B2 * | 11/2022 | Addison ............ A61B 5/14542 |
| 11,850,026 | B2 | 12/2023 | Levi et al. |
| 2002/0137464 | A1 | 9/2002 | Dolgonos et al. |
| 2004/0001633 | A1 | 1/2004 | Caviedes |
| 2004/0258285 | A1 | 12/2004 | Hansen et al. |
| 2005/0203348 | A1 | 9/2005 | Shihadeh et al. |
| 2007/0116328 | A1 | 5/2007 | Sablak et al. |
| 2008/0001735 | A1 | 1/2008 | Tran |
| 2008/0108880 | A1 | 5/2008 | Young et al. |
| 2008/0279420 | A1 | 11/2008 | Masticola et al. |
| 2008/0295837 | A1 | 12/2008 | McCormick et al. |
| 2009/0024012 | A1 | 1/2009 | Li et al. |
| 2009/0141124 | A1 | 6/2009 | Liu et al. |
| 2009/0304280 | A1 | 12/2009 | Aharoni et al. |
| 2010/0210924 | A1 | 8/2010 | Parthasarathy et al. |
| 2010/0236553 | A1 | 9/2010 | Jafari et al. |
| 2010/0249630 | A1 | 9/2010 | Droitcour et al. |
| 2010/0324437 | A1 | 12/2010 | Freeman et al. |
| 2011/0144517 | A1 | 6/2011 | Cervantes |
| 2011/0150274 | A1 | 6/2011 | Patwardhan et al. |
| 2012/0065533 | A1 | 3/2012 | Carrillo et al. |
| 2012/0075464 | A1 | 3/2012 | Derenne et al. |
| 2012/0195473 | A1 | 8/2012 | De Haan et al. |
| 2012/0243797 | A1 | 9/2012 | Di Venuto Dayer et al. |
| 2013/0073312 | A1 | 3/2013 | Thompson et al. |
| 2013/0267873 | A1 | 10/2013 | Fuchs |
| 2013/0271591 | A1 | 10/2013 | Van Leest et al. |
| 2013/0272393 | A1 | 10/2013 | Kirenko et al. |
| 2013/0275873 | A1 | 10/2013 | Shaw et al. |
| 2013/0324830 | A1 | 12/2013 | Bernal et al. |
| 2013/0324876 | A1 | 12/2013 | Bernal et al. |
| 2014/0023235 | A1 | 1/2014 | Cennini et al. |
| 2014/0052006 | A1 | 2/2014 | Lee et al. |
| 2014/0053840 | A1 | 2/2014 | Liu |
| 2014/0073860 | A1 | 3/2014 | Urtti |
| 2014/0139405 | A1 | 5/2014 | Ribble et al. |
| 2014/0140592 | A1 | 5/2014 | Lasenby et al. |
| 2014/0235976 | A1 | 8/2014 | Bresch et al. |
| 2014/0267718 | A1 | 9/2014 | Govro et al. |
| 2014/0272860 | A1 | 9/2014 | Peterson et al. |
| 2014/0275832 | A1 | 9/2014 | Muehlsteff et al. |
| 2014/0276104 | A1 | 9/2014 | Tao et al. |
| 2014/0330336 | A1 | 11/2014 | Errico et al. |
| 2014/0334697 | A1 | 11/2014 | Kersten et al. |
| 2014/0358017 | A1 | 12/2014 | Op Den Buijs et al. |
| 2014/0378810 | A1 | 12/2014 | Davis et al. |
| 2014/0379369 | A1 | 12/2014 | Kokovidis et al. |
| 2015/0003723 | A1 | 1/2015 | Huang et al. |
| 2015/0068069 | A1 | 3/2015 | Tran et al. |
| 2015/0094597 | A1 | 4/2015 | Mestha et al. |
| 2015/0131880 | A1 | 5/2015 | Wang et al. |
| 2015/0157269 | A1 | 6/2015 | Lisogurski et al. |
| 2015/0198707 | A1 | 7/2015 | Al-Alusi |
| 2015/0223731 | A1 | 8/2015 | Sahin |
| 2015/0238150 | A1 | 8/2015 | Subramaniam |
| 2015/0265187 | A1 | 9/2015 | Bernal et al. |

(56) References Cited

U.S. PATENT DOCUMENTS

| | | |
|---|---|---|
| 2015/0282724 A1 | 10/2015 | McDuff et al. |
| 2015/0286779 A1 | 10/2015 | Bala et al. |
| 2015/0301590 A1 | 10/2015 | Furst et al. |
| 2015/0317814 A1 | 11/2015 | Johnston et al. |
| 2015/0379370 A1 | 12/2015 | Clifton et al. |
| 2016/0000335 A1 | 1/2016 | Khachaturian et al. |
| 2016/0049094 A1 | 2/2016 | Gupta et al. |
| 2016/0082222 A1 | 3/2016 | Garcia Molina et al. |
| 2016/0140828 A1 | 5/2016 | Deforest |
| 2016/0143598 A1 | 5/2016 | Rusin et al. |
| 2016/0151022 A1 | 6/2016 | Berlin et al. |
| 2016/0156835 A1 | 6/2016 | Ogasawara et al. |
| 2016/0174887 A1 | 6/2016 | Kirenko et al. |
| 2016/0210747 A1 | 7/2016 | Hay et al. |
| 2016/0235344 A1 | 8/2016 | Auerbach |
| 2016/0310084 A1 | 10/2016 | Banerjee et al. |
| 2016/0317041 A1 | 11/2016 | Porges et al. |
| 2016/0345931 A1 | 12/2016 | Xu et al. |
| 2016/0367186 A1 | 12/2016 | Freeman et al. |
| 2017/0007342 A1 | 1/2017 | Kasai et al. |
| 2017/0007795 A1 | 1/2017 | Pedro et al. |
| 2017/0055877 A1 | 3/2017 | Niemeyer |
| 2017/0065484 A1 | 3/2017 | Addison et al. |
| 2017/0071516 A1 | 3/2017 | Bhagat et al. |
| 2017/0095215 A1 | 4/2017 | Watson et al. |
| 2017/0095217 A1 | 4/2017 | Hubert et al. |
| 2017/0119340 A1 | 5/2017 | Nakai et al. |
| 2017/0147772 A1 | 5/2017 | Meehan et al. |
| 2017/0164904 A1 | 6/2017 | Kirenko |
| 2017/0172434 A1 | 6/2017 | Amelard et al. |
| 2017/0173262 A1 | 6/2017 | Veltz |
| 2017/0238805 A1 | 8/2017 | Addison et al. |
| 2017/0238842 A1 | 8/2017 | Jacquel et al. |
| 2017/0311887 A1 | 11/2017 | Leussler et al. |
| 2017/0319114 A1 | 11/2017 | Kaestle |
| 2018/0042486 A1 | 2/2018 | Yoshizawa et al. |
| 2018/0042500 A1 | 2/2018 | Liao et al. |
| 2018/0049669 A1 | 2/2018 | Vu et al. |
| 2018/0053392 A1 | 2/2018 | White et al. |
| 2018/0104426 A1 | 4/2018 | Oldfield et al. |
| 2018/0106897 A1 | 4/2018 | Shouldice et al. |
| 2018/0169361 A1 | 6/2018 | Dennis et al. |
| 2018/0217660 A1 | 8/2018 | Dayal et al. |
| 2018/0228381 A1 | 8/2018 | Leboeuf et al. |
| 2018/0303351 A1 | 10/2018 | Mestha et al. |
| 2018/0310844 A1 | 11/2018 | Tezuka et al. |
| 2018/0325420 A1 | 11/2018 | Gigi |
| 2018/0333050 A1 | 11/2018 | Greiner et al. |
| 2018/0333102 A1 | 11/2018 | De Haan et al. |
| 2018/0352150 A1 | 12/2018 | Purwar et al. |
| 2019/0050985 A1 | 2/2019 | Den Brinker et al. |
| 2019/0133499 A1 | 5/2019 | Auerbach |
| 2019/0142274 A1 | 5/2019 | Addison et al. |
| 2019/0199970 A1 | 6/2019 | Greiner et al. |
| 2019/0209046 A1 | 7/2019 | Addison et al. |
| 2019/0209083 A1 | 7/2019 | Wu et al. |
| 2019/0307365 A1 | 10/2019 | Addison et al. |
| 2019/0311101 A1 | 10/2019 | Nienhouse |
| 2019/0343480 A1 | 11/2019 | Shute et al. |
| 2019/0380599 A1 | 12/2019 | Addison et al. |
| 2019/0380807 A1 | 12/2019 | Addison et al. |
| 2020/0046302 A1 | 2/2020 | Jacquel et al. |
| 2020/0187827 A1 | 6/2020 | Addison et al. |
| 2020/0202154 A1 | 6/2020 | Wang et al. |
| 2020/0205734 A1 | 7/2020 | Mulligan et al. |
| 2020/0237225 A1 | 7/2020 | Addison et al. |
| 2020/0242790 A1 | 7/2020 | Addison et al. |
| 2020/0250406 A1 | 8/2020 | Wang et al. |
| 2020/0253560 A1 | 8/2020 | De Haan |
| 2020/0279464 A1 | 9/2020 | Llewelyn |
| 2020/0289024 A1 | 9/2020 | Addison et al. |
| 2020/0329976 A1 | 10/2020 | Chen et al. |
| 2020/0409383 A1 | 12/2020 | Maunder |
| 2021/0068670 A1 | 3/2021 | Redtel |
| 2021/0142874 A1 | 5/2021 | Llewelyn |
| 2021/0153746 A1 | 5/2021 | Addison et al. |
| 2021/0201517 A1 | 7/2021 | Yang et al. |
| 2021/0233631 A1 | 7/2021 | Llewelyn |
| 2021/0235992 A1 | 8/2021 | Addison |
| 2021/0295662 A1 | 9/2021 | Bugbee et al. |
| 2021/0313075 A1 | 10/2021 | Mc Namara et al. |
| 2022/0211296 A1 | 7/2022 | Addison et al. |
| 2023/0122367 A1 | 4/2023 | Tesar |

FOREIGN PATENT DOCUMENTS

| | | |
|---|---|---|
| CN | 111728602 A | 10/2020 |
| CN | 112233813 A | 1/2021 |
| DE | 19741982 A1 | 10/1998 |
| EP | 2793189 B1 | 11/2016 |
| EP | 2428162 B1 | 8/2017 |
| EP | 3207862 A1 | 8/2017 |
| EP | 3207863 A1 | 8/2017 |
| EP | 3384827 A1 | 10/2018 |
| EP | 2772828 B1 | 1/2019 |
| JP | 2004173010 A | 6/2004 |
| JP | 2004283373 A | 10/2004 |
| JP | 3744778 B2 | 12/2005 |
| JP | 2009544080 A | 12/2009 |
| JP | 2011130996 A | 7/2011 |
| KR | 101644843 B1 | 8/2016 |
| RS | 20120373 A1 | 4/2014 |
| WO | 2004100067 A2 | 11/2004 |
| WO | 2005079658 A2 | 9/2005 |
| WO | 2010034107 A1 | 4/2010 |
| WO | 2010036653 A1 | 4/2010 |
| WO | 2015059700 A1 | 4/2015 |
| WO | 2015078735 A1 | 6/2015 |
| WO | 2015110859 A1 | 7/2015 |
| WO | 2016065411 A1 | 5/2016 |
| WO | 2016178141 A1 | 11/2016 |
| WO | 2016209491 A1 | 12/2016 |
| WO | 2017060463 A1 | 4/2017 |
| WO | 2017089139 A1 | 6/2017 |
| WO | 2017100188 A2 | 6/2017 |
| WO | 2017144934 A1 | 8/2017 |
| WO | 2018042376 A1 | 3/2018 |
| WO | 2019094893 A1 | 5/2019 |
| WO | 2019135877 A1 | 7/2019 |
| WO | 2019240991 A1 | 12/2019 |
| WO | 2020033613 A1 | 2/2020 |
| WO | 2021044240 A1 | 3/2021 |

OTHER PUBLICATIONS

Lai, C.J., et al., "Heated humidified high-flow nasal oxygen prevents intraoperative body temperature decrease in non-intubated thoracoscopy", Journal of Anesthesia, Oct. 15, 2018, 8 pages.

Lawrence, E., et al., "Data Collection, Correlation and Dissemination of Medical Sensor information in a WSN", IEEE 2009 Fifth International Conference on Networking and Services, 978-0-7695-3586-9/09, Apr. 20, 2009, pp. 402-408, 7 pages.

Li, et al., "A Non-Contact Vision-Based System for Respiratory Rate Estimation", IEEE 978-1-4244-7929-0/14, 2014, pp. 2119-2122, 4 pages.

Liu, H., et al., "A Novel Method Based on Two Cameras for Accurate Estimation of Arterial Oxygen Saturation", BioMedical Engineering Online, vol. 14, No. 52, 2015, 18 pages.

Liu, S., et al., "In-bed pose estimation: Deep learning with shallow dataset. IEEE journal of translational engineering in health and medicine", IEEE Journal of Translational Engineering in Health and Medicine, No. 7, 2019, pp. 1-12, 12 pages.

Liu, C., et al., "Motion Magnification", ACM Transactions on Graphics (TOG), vol. 24, No. 3, 2005, pp. 519-526, 8 pages.

LV, et al., "Class Energy Image Analysis for Video Sensor-Based Gait Recognition: A Review", Sensors, No. 15, 2015, pp. 932-964, 33 pages.

McDuff, Daniel J., et al., "A Survey of Remote Optical Photoplethysmographic Imaging Methods", IEEE 987-1-4244-0270-1/15, 2015, pp. 6398-6404, 7 pages.

(56) References Cited

OTHER PUBLICATIONS

Mestha, L.K., et al., "Towards Continuous Monitoring of Pulse Rate in Neonatal Intensive Care Unit with a Webcam", Proc. of 36th Annual Int. Conf. of the IEEE Engineering in Medicine and Biology Society, Chicago, IL, 2014, pp. 3817-3820, 4 pages.
Mukherjee, S., et al., "Patient health management system using e-health monitoring architecture", IEEE, International Advance Computing Conference (IACC), 978-1-4799-2572-8/14, Feb. 21, 2014, pp. 400-405, 6 pages.
Nguyen, et al., "3D shape, deformation and vibration measurements using infrared Kinect sensors and digital image correlation", Applied Optics, vol. 56, No. 32, Nov. 10, 2017, 8 pages.
Ni, et al., "RGBD-Camera Based Get-Up Event Detection for Hospital Fall Prevention", Acoustics, Speech and Signal Processing (ICASSP) 2012 IEEE International Conf., Mar. 2012, pp. 1405-1408, 6 pages.
Nisar, et al., "Contactless heart rate monitor for multiple persons in a video", IEEE International Conference on Consumer Electronics—Taiwan (ICCE-TW), XP03291229 [Retreived on Jul. 25, 2016], May 27, 2016, 2 pages.
Pereira, C., et al., "Noncontact Monitoring of Respiratory Rate in Newborn Infants Using Thermal Imaging", IEEE Transactions on Biomedical Engineering, Aug. 23, 2018, 10 pages.
Poh, et al., "Advancements in Noncontact, Multiparameter Physiological Measurements Using a Webcam", IEEE Transactions on Biomedical Engineering, vol. 58, No. 1, Jan. 2011, pp. 7-11, 5 pages.
Poh, et al., "Non-contact, automated cardiac pulse measurements using video imaging and blind source separation", OPT. Express 18, 2010, pp. 10762-10774, 14 pages.
Povsic, Klemen, et al., "Real-Time 3D visualization of the thoracoabdominal surface during breathing with body movement and deformation extraction", Physiological Measurement, vol. 36, No. 7, May 28, 2015, pp. 1497-1516, 22 pages.
Prochazka, et al., "Microsoft Kinect Visual and Depth Sensors for Breathing and Heart Rate Analysis", Senors, vol. 16, No. 7, Jun. 28, 2016, 11 pages.
Rajan, V., et al., "Clinical Decision Support for Stroke using Multiview Learning based Models for NIHSS Scores", PAKDD 2016 Workshop: Predictive Analytics in Critical Care (PACC), Auckland, New Zealand, 2016, pp. 190-199, 10 pages.
Rajan, V., et al., "Dependency Clustering of Mixed Data with Gaussian Mixture Copulas", 25th International Joint Conference on Artificial Intelligence IJCAI, New York, USA, 2016, pp. 1967-1973, 7 pages.
Reisner, A., et al., "Utility of the Photoplethysmogram in Circulatory Monitoring", American Society of Anesthesiologist, May 2008, pp. 950-958, 9 pages.
Reyes, B.A., et al., "Tidal Volume and Instantaneous Respiration Rate Estimation using a Volumetric Surrogate Signal Acquired via a Smartphone Camera", IEEE Journal of Biomedical and Health Informatics, vol. 21(3), Feb. 25, 2016, pp. 764-777, 15 pages.
Rougier, Caroline, et al., "Robust Video Surveillance for Fall Detection Based on Human Shape Deformation", IEEE Transactions on Circuits and Systems for Video Technology, vol. 21, No. 5, May 2011, pp. 611-622, 12 pages.
Rubinstein, M, "Analysis and Visualization of Temporal Variations in Video", Department of Electrical Engineering and Computer Science, Massachusetts Institute of Technology, Feb. 2014, 118 pages.
Scalise, Lorenzo, et al., "Heart rate measurement in neonatal patients using a webcamera", Department of Industrial Engineering and Mathematical Science, Italy, 978-1-4673-0882-3/12, EEE, 2012, 4 pages.
Schaerer, J., et al., "Multi-dimensional respiratory motion tracking from markerless optical surface imaging based on deformable mesh registration", Physics in Medicine and Biology, vol. 57, No. 2, Dec. 14, 2011, pp. 357-373, 18 pages.
Sengupta, A., et al., "A Statistical Model for Stroke Outcome Prediction and Treatment Planning", 38th Annual International Conference of the IEE Engineering in Medicine and Biology (Society IEEE EMBC2016), Orlando, USA, 2016, pp. 2516-2519, 4 pages.
Shah, Nitin, et al., "Performance of three new-generation pulse oximeters during motion and low perfursion in volunteers", Journal of Clinical Anesthesia, No. 24, 2012, pp. 385-391, 7 pages.
Shao, Dangdang, et al., "Noncontact Monitoring Breathing Pattern, Exhalation Flow Rate and Pulse Transit Time", EEE Transactions on Biomedical Engineering, vol. 61, No. 11, Nov. 2014, pp. 2760-2767, 8 pages.
Shrivastava, H., et al., "Classification with Imbalance: A Similarity-based Method for Predicting Respiratory Failure", IEEE International Conference on Bioinformatics and Biomedicine (IEEE BIBM2015), Washington, DC, USA, 2015, pp. 707-714, 8 pages.
Srinivas, J., et al., "A Mutual Authentication Framework for Wireless Medical Sensor Networks", Journal of Medical Systems, 41:80, 2017, pp. 1-19, 19 pages.
Sun, Yu, et al., "Motion-compensated noncontact imaging photoplethysmography to monitor cardiorespiratory status during exercise", Journal of Biomedical Optics, vol. 16, No. 7, Jul. 1, 2011, 10 pages.
Sun, Yu, et al., "Noncontact imaging photoplethysmography to effectively access pulse rate variability", Journal of Biomedical Optics, vol. 18(6), Jun. 2013, 10 pages.
Tamura, et al., "Wearable Photoplethysmographic Sensors—Past & Present", Electronics, vol. 3, 2014, pp. 282-302, 21 pages.
Tarassenko, L., et al., "Non-contact video-based vital sign monitoring using ambient light and auto-regressive models", Institute of Physics and Engineering in Medicine, vol. 35, 2014, pp. 807-831, 26 pages.
Teichmann, D., et al., "Non-Contact monitoring techniques—Principles and applications", In Proc. of IEEE International Conference of the Engineering in Medicine and Biology Society (EMBC), San Diego, CA, 2012, pp. 1302-1305, 4 pages.
Transue, S., et al., "Real-time Tidal Volume Estimation using Iso-surface Reconstruction", 2016 IEEE First International Conference on Connected Health: Applications, Systems and Engineering Technologies (CHASE), Jun. 27, 2016, pp. 209-218, 10 pages.
Verkruysee, Wim, et al., "Calibration of Contactless Pulse Oximetry", Anesthesia & Analgesia, vol. 124, No. 1, Jan. 2017, pp. 136-145, 10 pages.
Villarroel, Mauricio, et al., "Continuous non-contact vital sign monitoring in neonatal intensive care unit", Healthcare Technology Letters, vol. 1, Issue 3, 2014, pp. 87-91, 5 pages.
Wadhwa, N., et al., "Phase-Based Video Motion Processing", MIT Computer Science and Artificial Intelligence Lab, Jul. 2013, 9 pages.
Wadhwa, N., et al., "Riesz pyramids for fast phase-based video magnification", In Proc. of IEEE International Conference on Computational Photography (ICCP), Santa Clara, CA, 2014, 10 pages.
Wang, W., et al., "Exploiting spatial redundancy of image sensor for motion robust rPPG", IEEE Transactions on Biomedical Engineering, vol. 62, No. 2, 2015, pp. 415-425, 11 pages.
Wu, H.Y., et al., "Eulerian video magnifcation for revealing subtle changes in the world", ACM Transactions on Graphics (TOG), vol. 31, No. 4, 2012, pp. 651-658, 8 pages.
Wulbrand, H., et al., "Submental and diaphragmatic muscle activity during and at resolution of mixed and obstructive apneas and cardiorespiratory arousal in preterm infants", Pediatric Research, No. 38(3), 1995, pp. 298-305, 9 pages.
Yu, M.C., et al., "Noncontact Respiratory Measurement of Volume Change Using Depth Camera", 2012 Annual International Conference of the IEEE Engeineering in Medicine and Biology Society, Aug. 28, 2012, pp. 2371-2374, 4 pages.
Zaunseder, et al., "Spatio-temporal analysis of blood perfusion by imaging photoplethysmography", Progress in Biomedical Optics and Imaging, SPIE-International Society for Optical Engineering, vol. 10501, Feb. 20, 2018, 15 pages.
Zhou, J., et al., "Maximum parsimony analysis of gene copy number changes in tumor phylogenetics", 15th International Workshop on Algorithms in Bioinformatics WABI 2015, Atlanta, USA, 2015, pp. 108-120, 13 pages.

(56) References Cited

OTHER PUBLICATIONS

Rezaei, Mahdi, et al., "DeepSOCIAL: Social Distancing Monitoring and Infection Risk Assessment in COVID-19 Pandemic", Applied Sciences, vol. 10, 7514, Oct. 26, 2020, pp. 1-29, 29 pages.
Sathyamoorthy, Adarsh Jagan, et al., "COVID-Robot: Monitoring Social Distancing Constraints in Crowded Scenarios", Aug. 21, 2020, pp. 1-11, 11 pages.
Liu, X., et al., "An Image Captioning Method for Infant Sleeping Environment Diagnosis", Springer International Publishing, May 15, 2019, pp. 18-26, 9 pages.
Sokooti, Hess, et al., "Hierarchical Prediction of Registration Misalignment Using a Convolutional LSTM: Application to Chest CT Scans", IEEE Access, IEEE, USA, vol. 9, Apr. 20, 2021, 62008-62020, 13 pages.
"European Search Report", European Application No. 17156334.9, Applicant: Covidien LP, Aug. 23, 2017, 10 pages.
"European Search Report", European Patent Application No. 17156337.2, Applicant: Covidien LP, Aug. 23, 2017, 10 pages.
"International Search Report and Written Opinion", International Application No. PCT/US2021/015669, Apr. 12, 2021, 15 pages.
"International Search Report and Written Opinion", International Application No. PCT/US2018/060648, Jan. 28, 2019, 17 pages.
"International Search Report and Written Opinion", International Application No. PCT/US2018/065492, Mar. 8, 2019, 12 pages.
"International Search Report and Written Opinion", International Application No. PCT/US2019/035433, Nov. 11, 2019, 17 pages.
"International Search Report and Written Opinion", International Application No. PCT/US2019/045600, Oct. 23, 2019, 19 pages.
"Invitation to Pay Additional Fees and Partial International Search Report", International Application No. PCT/US2019/035433, Sep. 13, 2019, 16 pages.
"Medical Electrical Equipment, Part 2-61: Particular requirements for basic safety and essential performance of pulse oximeter equipment", BSI Standards Publication, BS EN ISO 80601-2-61, 2011, 98 pages.
Aarts, Lonneke A.M., et al., "Non-contact heart rate monitoring utilizing camera photoplethysmography in neonatal intensive care unit—A Pilot Study", Early Human Development 89, 2013, pp. 943-948, 6 pages.
Abbas, A.K., et al., "Neonatal non-contact respiratory monitoring based on real-time infrared thermography", Biomed. Eng. Online, vol. 10, No. 93, 2011, 17 pages.
Addison, Paul S., "A Review of Signal Processing Used in the Implementation of the Pulse Oximetry Photoplethysmographic Fluid Responsiveness Parameter", International Anesthesia Research Society, vol. 119, No. 6, Dec. 2014, pp. 1293-1306, 14 pages.
Addison, Paul S., et al., "Developing an algorithm for pulse oximetry derived respirator rate (RRoxi): a healthy volunteer study", J Clin comput, No. 26, 2012, pp. 45-51, 7 pages.
Addison, Paul S., et al., "Pulse oximetry-derived respiratory rate in general care floor patients", J. Clin Monit Comput, No. 29, 2015, pp. 113-120, 8 pages.
Addison, P.S., et al., "Video-based Heart Rate Monitoring across a Range of Skin Pigmentations during an Acute Hypoxic Challenge", J Clin Monit Comput, vol. 9, Nov. 9, 2017, 15 pages.
Al-Naji, Ali, et al., "Real Time Apnoea Monitoring of Children Using the Microsoft Kinect Sensor: A Pilot Study", Sensors, 17(286), Feb. 3, 2017, 15 pages.
Amazon, "Dockem Koala Tablet Wall Mount Dock for iPad Air/Mini/Pro, Samsung Galaxy Tab/Note, Nexus 7/10, and More (Black Brackets, Screw-in Version)", https://www.amazon.com/Tablet-Dockem-Samsung-Brackets-Version-dp/B00JV75FC6?th=1, First available Apr. 22, 2014, viewed on Nov. 16, 2021, Apr. 22, 2014, 4 pages.
Amelard, et al., "Non-contact transmittance photoplethysmographic imaging (PPGI) for long-distance cardiovascular monitoring", ResearchGate, XP055542534 [Retrieved online Jan. 15, 2019], Mar. 23, 2015, pp. 1-13, 14 pages.

Armanian, A. M., "Caffeine administration to prevent apnea in very premature infants", Pediatrics & Neonatology, 57(5), 2016, pp. 408-412, 5 pages.
Barone, S, et al., "Computer-aided modelling of three-dimensional maxillofacial tissues through multi-modal imaging", Proceedings of the Institution of Mechanical Engineers, Journal of Engineering in Medicine, Part H vol. 227, No. 2, Feb. 1, 2013, 1 page.
Barone, S, et al., "Creation of 3D Multi-body Orthodontic Models by Using Independent Imaging Sensors", Senros MDPI AG Switzerland, vol. 13, No. 2, Jan. 1, 2013, pp. 2033-2050, 18 pages.
Bartula, M., et al., "Camera-based System for Sontactless Monitoring of Respiration", 2013 35th Annual International Conference of the IEEE Engineering in Medicine and Biology Society (EMBC), Jul. 3, 2013, pp. 2672-2675, 4 pages.
Bhattacharya, S., et al., "A Novel Classification Method for Predicting Acute Hypotensive Episodes in Critical Care", 5th ACM Conference on Bioinformatics, Computational Bilogy and Health Informatics (ACM-BCB 2014), Newport Beach, USA, 2014, 10 pages.
Bhattacharya, S., et al., "Unsupervised learning using Gaussian Mixture Copula models", 21st International Conference on Computational Statistics (COMPSTAT 2014), Geneva, Switzerland, 2014, pp. 523-530, 8 pages.
Bickler, Philip E., et al., "Factors Affecting the Performance of 5 Cerebral Oximeters During Hypoxia in Healthy Volunteers", Society for Technology in Anesthesia, vol. 117, No. 4, Oct. 2013, pp. 813-823, 11 pages.
Bousefsaf, Frederic, et al., "Continuous wavelet filtering on webcam photoplethysmographic signals to remotely assess the instantaneous heart rate", Biomedical Signal Processing and Control 8, 2013, pp. 568-574, 7 pages.
Bruser, C., et al., "Adaptive Beat-to-Beat Heart Rate Estimation in Ballistocardiograms", IEEE Transactions Information Technology in Biomedicine, vol. 15, No. 5, Sep. 2011, pp. 778-786, 9 pages.
Cennini, Giovanni, et al., "Heart rate monitoring via remote photoplethysmography with motion artifacts reduction", Optics Express, vol. 18, No. 5, Mar. 1, 2010, pp. 4867-4875, 9 pages.
Colantonio, S., et al., "A smart mirror to promote a healthy lifestyle", Biosystems Engineering. vol. 138, Innovations in Medicine and Healthcare, Oct. 2015, pp. 33-43, 11 pages.
Cooley, et al., "An Alorithm for the Machine Calculation of Complex Fourier Series", Aug. 17, 1964, pp. 297-301, 5 pages.
Di Fiore, J.M., et al., "Intermittent hypoxemia and oxidative stress in preterm infants", Respiratory Physiology & Neurobiology, No. 266, 2019, pp. 121-129, 25 pages.
Fei, J., et al., "Thermistor at a distance: unobtrusive measurement of breathing", IEEE Transactions on Biomedical Engineering, vol. 57, No. 4, 2010, pp. 968-998, 11 pages.
Feng, Litong, et al., "Dynamic ROI based on K-means for remote photoplethysmography", IEE International Conference on Accoustics, Speech and Signal Processing (ICASSP), Apr. 2015, pp. 1310-1314, 5 pages.
Fischer, et al., "ReMoteCare: Health Monitoring with Streaming Video", OCMB '08, 7th International Conference on Mobile Business, IEEE, Piscataway, NJ,, Jul. 7, 2008, pp. 280-286.
George, et al., "Respiratory Rate Measurement From PPG Signal Using Smart Fusion Technique", International Conference on Engineering Trends and Science & Humanities (ICETSH-2015), 2015, 5 pages.
Goldman, L.J., "Nasal airflow and thoracoabdominal motion in children using infrared thermographic video processing", Pediatric Pulmonology, vol. 47, No. 5, 2012, pp. 476-486, 11 pages.
Grimm, T., et al., "Sleep position classification from a depth camera using bed aligned maps", 23rd International Conference on Pattern Recognition (ICPR), Dec. 2016, pp. 319-324, 6 pages.
GSMARENA, "Apple iPad Pro 11 (2018)", https://www.gsmarena.com/apple_ipad_pro_11_(2018)-9386.pjp, viewed on Nov. 16, 2021, 1 page.
Guazzi, Alessandro R., et al., "Non-contact measurement of oxygen saturation with an RGB camera", Biomedical Optics Express, vol. 6, No. 9, Sep. 1, 2015, pp. 3320-3338, 19 pages.

(56) References Cited

OTHER PUBLICATIONS

Han, J., et al., "Visible and infrared image registration in man-made environments employing hybrid visuals features", Pattern Recognition Letters, vol. 34, No. 1, 2013, pp. 42-51, 10 pages.

Harte, James M., et al., "Chest wall motion analysis in healthy volunteers and adults with cystic fibrosis using a novel Kinect-based motion tracking system", Medical & Biological Engineering & Computing, 54(11), Feb. 13, 2016, pp. 1631-1640, 11 pages.

Juddar, V., et al., "Predicting Postoperative Acute Respiratory Failure in Critical Care using Nursing Notes and Physiological Signals", 36th Annual International Conference of IEEE Engineering in Medicine and Biology Society (IEEE EMBC 2014), Chicago, USA, 2014, pp. 2702-2705, 4 pages.

Hyvarinen, A., et al., "Independent Component Analysis: Algorithms and Applications", Neural Networks, vol. 13, No. 4, 2000, pp. 411-430, 31 pages.

Javadi, M., et al., "Diagnosing Pneumonia in Rural Thailand: Digital Cameras versus Film Digitizers for Chest Radiograph Teleradiology", International Journal of Infectious Disease, 10(2), Mar. 2006, pp. 129-135, 7 pages.

Jopling, M. W., et al., "Issues in the Laboratory Evaluation of Pulse Oximeter Performance", Anesth. Analg., No. 94, 2002, pp. S62-S68, 7 pages.

Kastle, Siegfried W., et al., "Determining the Artifact Sensitivity of Recent Pulse Oximeters During Laboratory Benchmarking", Journal of Clinical Monitoring and Computing, vol. 16, No. 7, 2000, pp. 509-552, 14 pages.

Klaessens, J.H.G.M., et al., "Non-invasive skin oxygenation imaging using a multi-spectral camera system: Effectiveness of various concentration algorithms applied on human skin", Proc. of SPIE, vol. 7174 717408-1, 2009, 14 pages.

Kong, Lingqin, et al., "Non-contact detection of oxygen saturation based on visible light imaging device using ambient light", Optics Express, vol. 21, No. 15, Jul. 29, 2013, pp. 17646-17471, 8 pages.

Kortelainen, J.M., et al., "Sleep staging based on signals acquired through bed sensor", IEEE Transactions on Informational Technology in Biomedicine, vol. 14, No. 3, May 2010, pp. 776-785, 10 pages.

Kumar, M., et al., "Distance PPG: Robust non-contact vital signs monitoring using a camera", Biomedical Optics Express, vol. 6, No. 5, May 1, 2015, 24 pages.

\* cited by examiner

| ICG Information | RGB Information | Meaning |
|---|---|---|
| Strong | Strong | Region has strong flow and perfusion hence viable region of tissue |
| Strong | Weak or None | Region has possibly recently had blood flow cut off subsequent to ICG dye injection or be indicative of very low blood flow -- either way there may be a risk of hypoxia |
| Weak or None | Strong | Good RGB indication of perfusion but no ICG suggests ICG possibly injected at wrong site |
| Weak or None | Weak or None | No blood flow at this site risk and low perfusion hence possible risk of hypoxia |

Fig. 14

SYSTEMS AND METHODS FOR VIDEO-BASED PATIENT MONITORING DURING SURGERY

CROSS-REFERENCE TO RELATED APPLICATIONS

The present application is a continuation of U.S. Non-Provisional patent application Ser. No. 16/431,384 filed Jun. 4, 2019, which claims priority to U.S. Provisional Patent Application No. 62/685,485, filed Jun. 15, 2018, and U.S. Provisional Patent Application No. 62/695,244, filed Jul. 9, 2018, the disclosures of which are incorporated by reference herein in their entireties.

BACKGROUND

Many conventional medical monitors require attachment of a sensor to a patient in order to detect physiologic signals from the patient and to transmit detected signals through a cable to the monitor. These monitors process the received signals and determine vital signs such as the patient's pulse rate, respiration rate, and arterial oxygen saturation. For example, a pulse oximeter is a finger sensor that may include two light emitters and a photodetector. The sensor emits light into the patient's finger and transmits the detected light signal to a monitor. The monitor includes a processor that processes the signal, determines vital signs (e.g., pulse rate, respiration rate, arterial oxygen saturation), and displays the vital signs on a display.

Other monitoring systems include other types of monitors and sensors, such as electroencephalogram (EEG) sensors, blood pressure cuffs, temperature probes, air flow measurement devices (e.g., spirometer), and others. Some wireless, wearable sensors have been developed, such as wireless EEG patches and wireless pulse oximetry sensors.

Video-based monitoring is a field of patient monitoring that uses one or more remote video cameras to detect physical attributes of the patient. This type of monitoring may also be called "non-contact" monitoring in reference to the remote video sensor(s), which does/do not contact the patient. The remainder of this disclosure offers solutions and improvements in this field.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 14 is a table illustrating possible ICG and RGB information combinations and corresponding interpretations according to embodiments described herein.

DETAILED DESCRIPTION

Figure 1:
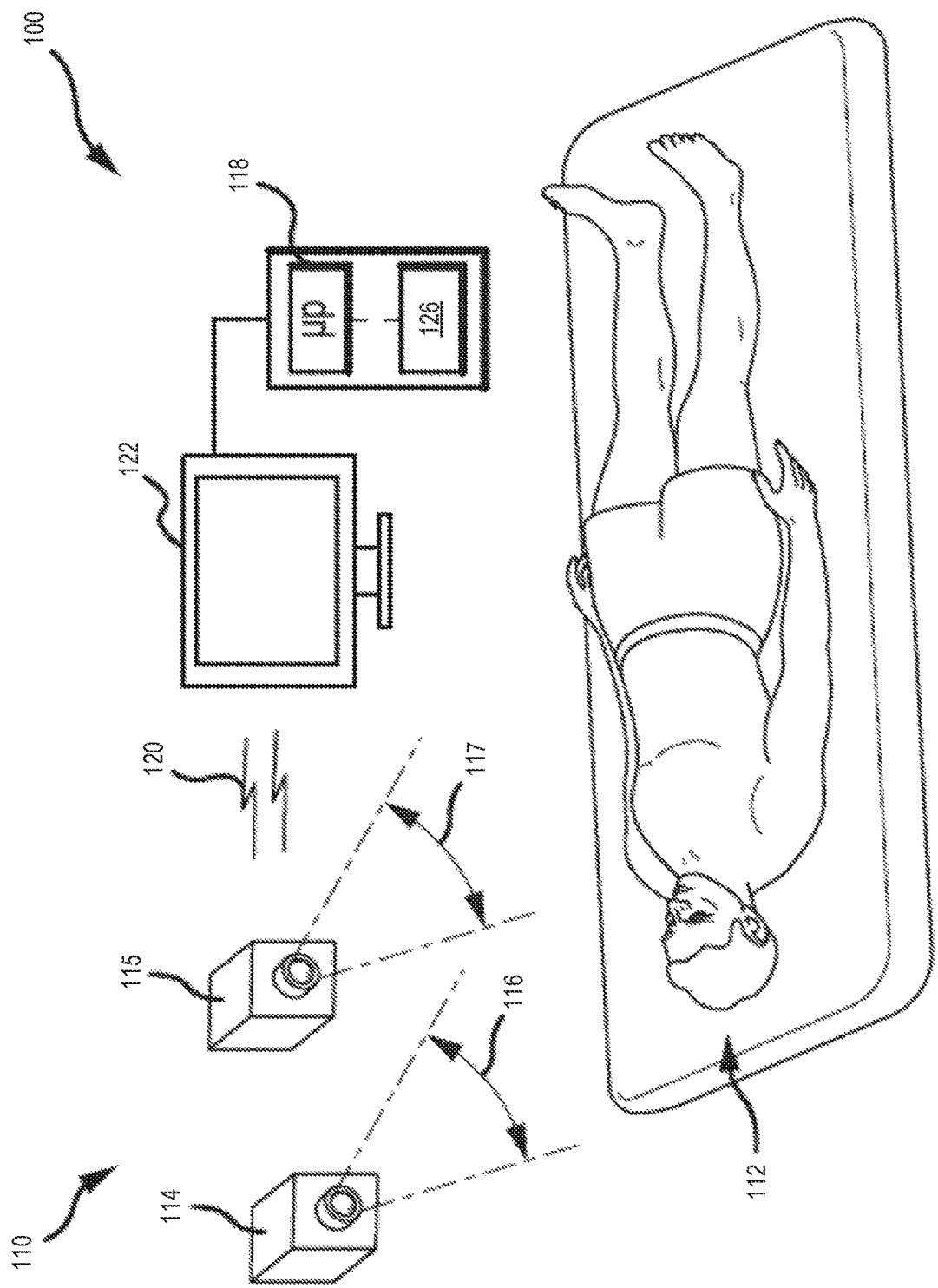
FIG. 1 is a schematic view of a video-based patient monitoring system according to various embodiments described herein.

The following disclosure describes video-based patient monitoring systems and associated methods for monitoring and/or assessing blood flow in a region of a patient during surgery. As described in greater detail below, systems and/or methods configured in accordance with embodiments of the present technology are configured to capture indocyanine green (ICG) images of a region of a patient to track ICG dye injected into the patient as an indication of blood flow in the region. Additionally, or alternatively, the systems and/or methods can be configured to capture RGB images of the region and/or to generate information pertaining to one or more parameters of blood flow in the region. In particular, the system and/or methods can be configured to generate an indication of pulsation, pulsation strength, and/or perfusion in the region as pixels in a sequence of RGB images change color. In these and other embodiments, the systems and/or methods can be configured to overlay the generated information onto the ICG images, for example, to provide a clinician a more complete indication of blood flow in the region.

ICG dye can be used to assess blood flow within a patient, such as to assess perfusion in a patient's organ, or to assess the return of proper blood flow to a region after surgery. In some systems and methods, blood flow in a region of a patient can be monitored by injecting ICG dye into the patient and using a tuned infrared light source and an IR camera to visually track the ICG dye. In particular, ICG dye can be injected upstream from the region, and blood can transport the ICG dye to and/or through the region. The presence of ICG dye in a part of the region indicates that the part is receiving blood flow from the site at which the ICG dye was injected. In this manner, the systems and methods can use the ICG dye to identify possible occlusions within the region by identifying parts of the region where no ICG dye is present.

There are, however, several limitations to use of ICG dye as an indication of blood flow within a patient. For example, ICG dye has a relatively short half-life in humans (e.g., three to four minutes depending on metabolic rates), meaning that more than one dosage is often required. Yet ICG dye dosage limits apply for humans (typically one or two dosages per session depending on body weight). In addition, ICG dye trapped at a site within a patient where blood flow is cut off takes longer to metabolize. Thus, ICG dye injected as a second dosage may not provide a good indication that blood flow has ceased at the site if ICG dye from a first dosage is still present and visible. Moreover, ICG equipment is expensive, and the costs of the ICG equipment are often passed to patients requiring its use. These costs are often exacerbated as the patient requires multiple ICG dye injections and/or sessions.

Video-based patient monitoring systems and associated methods in accordance with embodiments of the present technology are configured to monitor one or more parameters of blood flow (e.g., pulsation, pulsation strength, perfusion, etc.) in a region of the patient. In some embodiments, the systems and methods are configured to use these parameters to indicate sites in the region where blood flow has decreased and/or ceased. For example, the systems and methods can be used prior to injection of ICG dye to indicate sites in the region where blood flow has decreased and/or ceased. The systems and methods can then be configured to interrogate these sites with ICG dye to further assess whether occlusions are present at the sites. This can reduce the number of ICG dye injections required as a clinician can use a first injection of ICG dye to interrogate a specific site rather than search for potential occlusion sites.

In these and other embodiments, the systems and methods can be employed after the injection of ICG dye to use the one or more parameters of blood flow to indicate sites in the region where blood flow has decreased and/or ceased. For example, the systems and methods can indicate whether blood flow has decreased and/or ceased at a site where ICG dye from a first injection is still present. This can decrease the likelihood that the presence of ICG dye at a site (such as a site with slowed metabolism of ICG dye) leads a clinician to incorrectly conclude that there is blood flow to the site. In turn, with the present systems and methods, subsequent injections of ICG dye can provide a better indication of blood flow to and/or within a region. Thus, the video-based patient monitoring systems and associated methods disclosed herein have the potential to improve recordkeeping, improve patient care, reduce errors in vital sign measurements, increase frequency and accuracy of blood flow monitoring, help healthcare providers better characterize and respond to adverse medical conditions indicated by a decrease and/or cessation in blood flow, and generally improve monitoring of patients, along with many other potential advantages discussed below.

Specific details of several embodiments of the present technology are described herein with reference to FIGS. 1-14. Although many of the embodiments are described with respect to devices, systems, and methods for video-based patient monitoring of a human during surgery, other applications and other embodiments in addition to those described herein are within the scope of the present technology. For example, at least some embodiments of the present technology may be useful for video-based patient monitoring of other animals and/or for video-based patient monitoring outside of surgery, such as pre-surgery and/or post-surgery. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

FIG. 1 is a schematic view of a video-based patient monitoring system 100 and a patient 112 according to an embodiment of the invention. The system 100 includes a non-contact detector 110 placed remote from the patient 112. In some embodiments, the detector 110 can include one or more image capture devices, such as one or more video cameras. In the illustrated embodiment, the non-contact detector 110 includes a video camera 114 and a video camera 115. The cameras 114 and 115 are remote from the patient 112 in that they are spaced apart from and do not contact the patient 112. The cameras 114 and 115 each include a detector exposed to a field of view 116 and 117, respectively, that encompasses at least a portion of the patient 112.

The cameras 114 and 115 can capture a sequence of images over time. The cameras 114 and/or 115 can be a standard or scientific red, green, and blue (RGB) camera capable of capturing images with a specified (e.g., 8, 12, 16, etc.) bit depth per pixel. As described in greater detail below, color variations in the pixels of images captured by the cameras 114 and/or 115 can be used to generate pulsation and/or perfusion information of a region of interest. The cameras 114 and/or 115 can additionally or alternatively be infrared cameras configured to detect (e.g., via use of a filter) infrared (IR) light projected from a tuned IR light source and/or reflected off the patient 112. As described in greater detail below, the IR light can illuminate indocyanine green (ICG) dye injected into the patient 112. The presence of and/or variations in the ICG dye in images captured by the cameras 114 and/or 115 can be used to determine characteristics of blood flow in a region of interest. Although the cameras 114 and 115 are illustrated as separate image capture devices, the cameras 114 and 115 can be combined into a single image capture device in other embodiments of the present technology.

Figure 2:
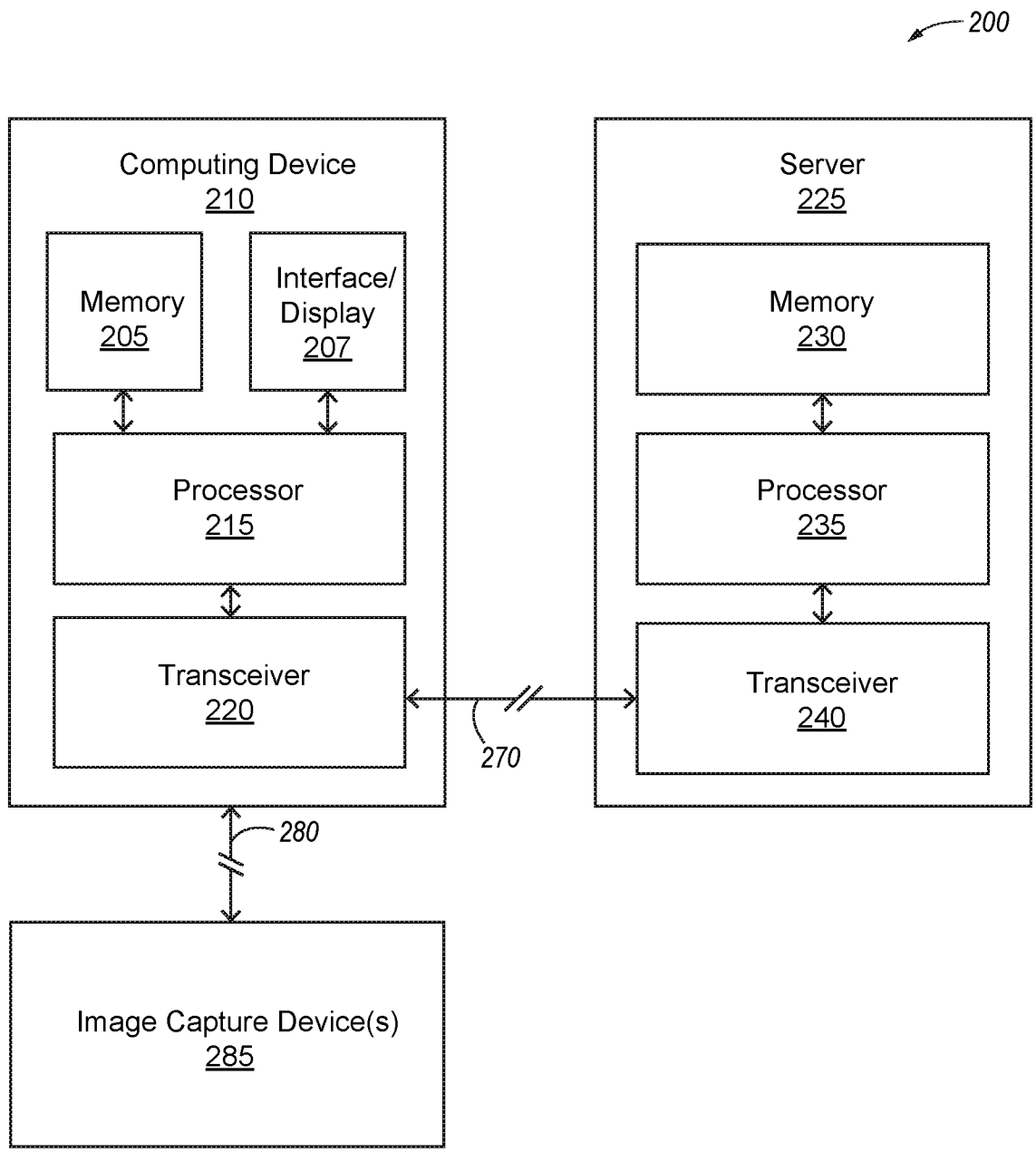
FIG. 2 is a block diagram illustrating a video-based patient monitoring system having a computing device, a server, and one or more image capture devices according to various embodiments described herein.

The detected images can be sent to a computing device through a wired or wireless connection 120. The computing device can include a processor 118 (e.g., a microprocessor), a display 122, and/or hardware memory 126 for storing software and computer instructions. Sequential image frames of the patient are recorded by the video camera(s) 114 and/or 115 and sent to the processor 118 for analysis. The display 122 may be remote from the camera(s) 114 and/or 115, such as a video screen positioned separately from the processor and memory. As described in greater detail below, the display 122 can be a display, such as a goggle headset, configured for augmented, virtual, and/or mixed reality. Other embodiments of the computing device may have different, fewer, or additional components than shown in FIG. 1. In some embodiments, the computing device may be a server. In other embodiments, the computing device of FIG. 1 may be additionally connected to a server (e.g., as shown in FIG. 2 and discussed in greater detail below). The captured images/video can be processed or analyzed at the computing device and/or a server to determine a variety of parameters (e.g., pulsation, pulsation strength, perfusion, etc.) of the patient 112, as disclosed herein.

FIG. 2 is a block diagram illustrating a video-based patient monitoring system 200 having a computing device 210, a server 225, and one or more image capture devices 285 according to various embodiments of the invention. In various embodiments, fewer, additional, and/or different components may be used in the system 200. The computing device 210 includes a processor 215 that is coupled to a memory 205. The processor 215 can store and recall data and applications in the memory 205, including applications that process information and send commands/signals according to any of the methods disclosed herein. The processor 215 may also (i) display objects, applications, data, etc. on an interface/display 207 and/or (ii) receive inputs through the interface/display 207. As shown, the processor 215 is also coupled to a transceiver 220.

The computing device 210 can communicate with other devices, such as the server 225 and/or the image capture device(s) 285 via (e.g., wired or wireless) connections 270 and/or 280, respectively. For example, the computing device 210 can send to the server 225 information determined about a patient from images captured by the image capture device(s) 285. The computing device 210 may be the computing device of FIG. 1. Accordingly, the computing device 210 may be located remotely from the image capture device(s) 285, or it may be local and close to the image capture device(s) 285 (e.g., in the same room). In various embodiments disclosed herein, the processor 215 of the computing device 210 may perform the steps disclosed herein. In other embodiments, the steps may be performed on a processor 235 of the server 225. In some embodiments, the various steps and methods disclosed herein may be performed by both of the processors 215 and 235. In some embodiments, certain steps may be performed by the processor 215 while others are performed by the processor 235. In some embodiments, information determined by the processor 215 may be sent to the server 225 for storage and/or further processing.

In some embodiments, the image capture device(s) 285 are remote sensing device(s), such as video camera(s) as described above with respect to FIG. 1. In some embodiments, the image capture device(s) 285 may be or include some other type(s) of device(s), such as proximity sensors or proximity sensor arrays, heat or infrared sensors/cameras, sound/acoustic or radiowave emitters/detectors, or other devices that include a field of view and may be used to monitor the location and/or characteristics of a patient or a region of interest (ROI) of a patient. Body imaging technology may also be utilized according to the methods disclosed herein. For example, backscatter x-ray or millimeter wave scanning technology may be utilized to scan a patient, which can be used to define and/or monitor a ROI. Advantageously, such technologies may be able to "see" through clothing, bedding, or other materials while giving an accurate representation of the patient's skin. This may allow for more accurate measurements, particularly if the patient is wearing baggy clothing or is under bedding. The image capture device(s) 285 can be described as local because they are relatively close in proximity to a patient such that at least a part of a patient is within the field of view of the image capture device(s) 285. In some embodiments, the image capture device(s) 285 can be adjustable to ensure that the patient is captured in the field of view. For example, the image capture device(s) 285 may be physically movable, may have a changeable orientation (such as by rotating or panning), and/or may be capable of changing a focus, zoom, or other characteristic to allow the image capture device(s) 285 to adequately capture images of a patient and/or a ROI of the patient. In various embodiments, for example, the image capture device(s) 285 may focus on a ROI, zoom in on the ROI, center the ROI within a field of view by moving the image capture device(s) 285, or otherwise adjust the field(s) of view to allow for better and/or more accurate tracking/measurement of the ROI.

The server 225 includes a processor 235 that is coupled to a memory 230. The processor 235 can store and recall data and applications in the memory 230. The processor 235 is also coupled to a transceiver 240. In some embodiments, the processor 235, and subsequently the server 225, can communicate with other devices, such as the computing device 210 through the connection 270.

The devices shown in the illustrative embodiment may be utilized in various ways. For example, any of the connections 270 and 280 may be varied. Any of the connections 270 and 280 may be a hard-wired connection. A hard-wired connection may involve connecting the devices through a universal serial bus (USB) port, serial port, parallel port, or other type of wired connection that can facilitate the transfer of data and information between a processor of a device and a second processor of a second device. In another embodiment, any of the connections 270 and 280 may be a dock where one device may plug into another device. In other embodiments, any of the connections 270 and 280 may be a wireless connection. These connections may take the form of any sort of wireless connection, including, but not limited to, Bluetooth connectivity, Wi-Fi connectivity, infrared, visible light, radio frequency (RF) signals, or other wireless protocols/methods. For example, other possible modes of wireless communication may include near-field communications, such as passive radio-frequency identification (RFID) and active RFID technologies. RFID and similar near-field communications may allow the various devices to communicate in short range when they are placed proximate to one another. In yet another embodiment, the various devices may connect through an internet (or other network) connection. That is, any of the connections 270 and 280 may represent several different computing devices and network components that allow the various devices to communicate through the internet, either through a hard-wired or wireless connection. Any of the connections 270 and 280 may also be a combination of several modes of connection.

The configuration of the devices in FIG. 2 is merely one physical system 200 on which the disclosed embodiments may be executed. Other configurations of the devices shown may exist to practice the disclosed embodiments. Further, configurations of additional or fewer devices than the ones shown in FIG. 2 may exist to practice the disclosed embodiments. Additionally, the devices shown in FIG. 2 may be combined to allow for fewer devices than shown or separated such that more than the three devices exist in a system. It will be appreciated that many various combinations of computing devices may execute the methods and systems disclosed herein. Examples of such computing devices may include other types of medical devices and sensors, infrared cameras/detectors, night vision cameras/detectors, other types of cameras, augmented reality goggles, virtual reality goggles, mixed reality goggle, radio frequency transmitters/receivers, smart phones, personal computers, servers, laptop computers, tablets, blackberries, RFID enabled devices, smart watch or wearables, or any combinations of such devices.

Figure 3:
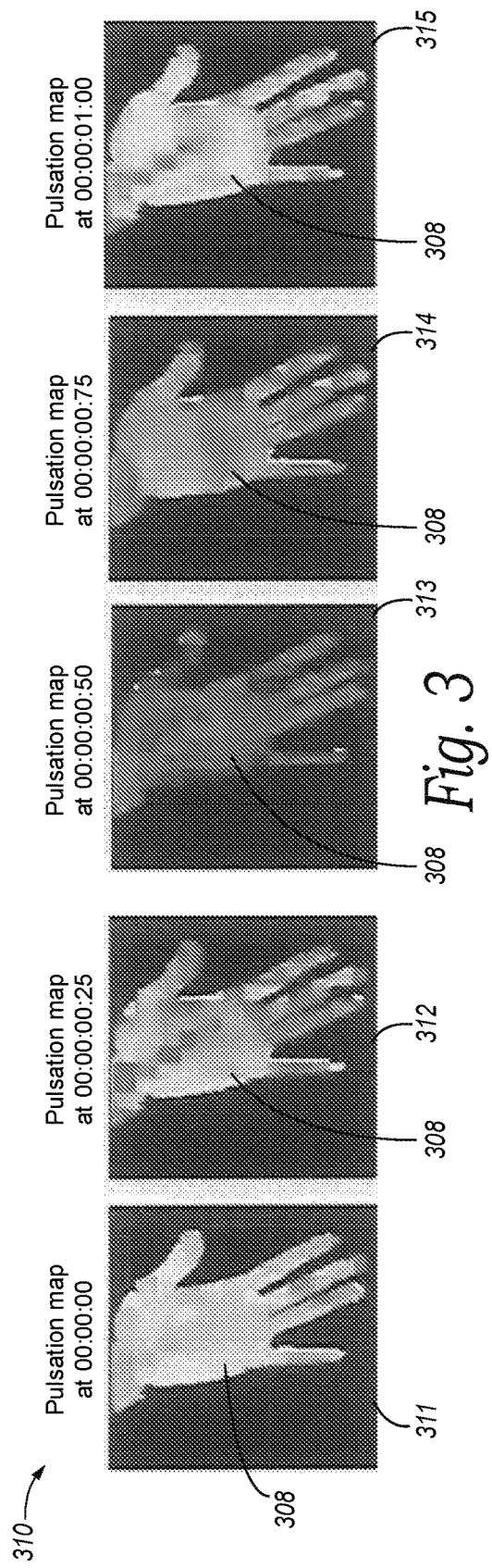
FIG. 3 is a sequence of pulsation images generated from red, green, and blue (RGB) images captured using an image capture device of a video-based patient monitoring system according to various embodiments described herein.

FIG. 3 is a sequence 310 of pulsation images 311-315 generated from RGB images captured using an image capture device (e.g., the RGB video camera 114 and/or 115 shown in FIG. 1 and/or an image capture device 285 shown in FIG. 2) of a video-based patient monitoring system. In particular, the sequence 310 of pulsation images 311-315 illustrates pulsation in a hand 308 of a patient (e.g., in real time) over a period of the patient's heartbeat (e.g., over approximately 1 second). In some embodiments, the system can generate the pulsation images 311-315 by directing the image capture device toward a region of the patient (e.g., the patient's hand 308) and capturing a sequence of standard RGB images as a video-photoplethysmogram signal. The system can then calculate a pulsation field from subtle color changes in the pixels of the RGB images over time. For example, the system can compute a difference between a first color value of a pixel in a first RGB image and a second color value of the same pixel in a second RGB image. The system can assign the pixel a color from a predetermined color scheme corresponding to the computed difference (e.g., corresponding to the sign and/or magnitude of the difference). The assigned color can then be displayed over the respective RGB image to visually depict pulsation at that site in a pulsation image (e.g., in real time). In an embodiment, the assigned colors (from the predetermined color scheme) exaggerate or emphasize the subtle changes detected by the system, to make the detected changes easier to see visually in real time.

As shown in FIG. 3, the backgrounds of the pulsation images 311-315 (i.e., the non-skin regions) are black because the corresponding pixels in the RGB images do not change color from one RGB image to the next and have been excluded with an image mask. The hand 308 varies in color across the field of view of the image capture device and across the sequence 310 of pulsation images 311-315. This variation in color indicates the pulsation information captured by and generated from color changes in the corresponding pixels of the RGB images. Thus, by assigning colors from a predetermined color scheme to the subtle color changes in the RGB images, the system can depict pulsation information of the hand 308 to a clinician in the pulsation images 311-315.

In some embodiments, the generated pulsation images (e.g., the images 311-315) and/or the corresponding RGB images can be used to determine the patient's heart rate. For example, the pulsation image 311 is generally identical to the pulsation image 315, indicating that the patient's heart was in a similar phase (e.g., a diastole phase or a systole phase) at the time the standard RGB images underlaying the pulsation images 311 and 315 were captured. Using the time elapsed between the two RGB images, the system can calculate a period of the patient's heartbeat and, in turn, the patient's heart rate. In these and other embodiments, the system can use a second signal of different colors in combination with the generated pulsation information to calculate oxygen saturation in the region of the patient. For example, two signals from the RGB camera (or multiple signals from any combination of monochrome cameras and filters) may be used to provide an indication of oxygen saturation using the standard ratio-of-ratio technique used in pulse oximetry (as described in more detail in co-pending application Ser. No. 15/432,057).

Figure 4:
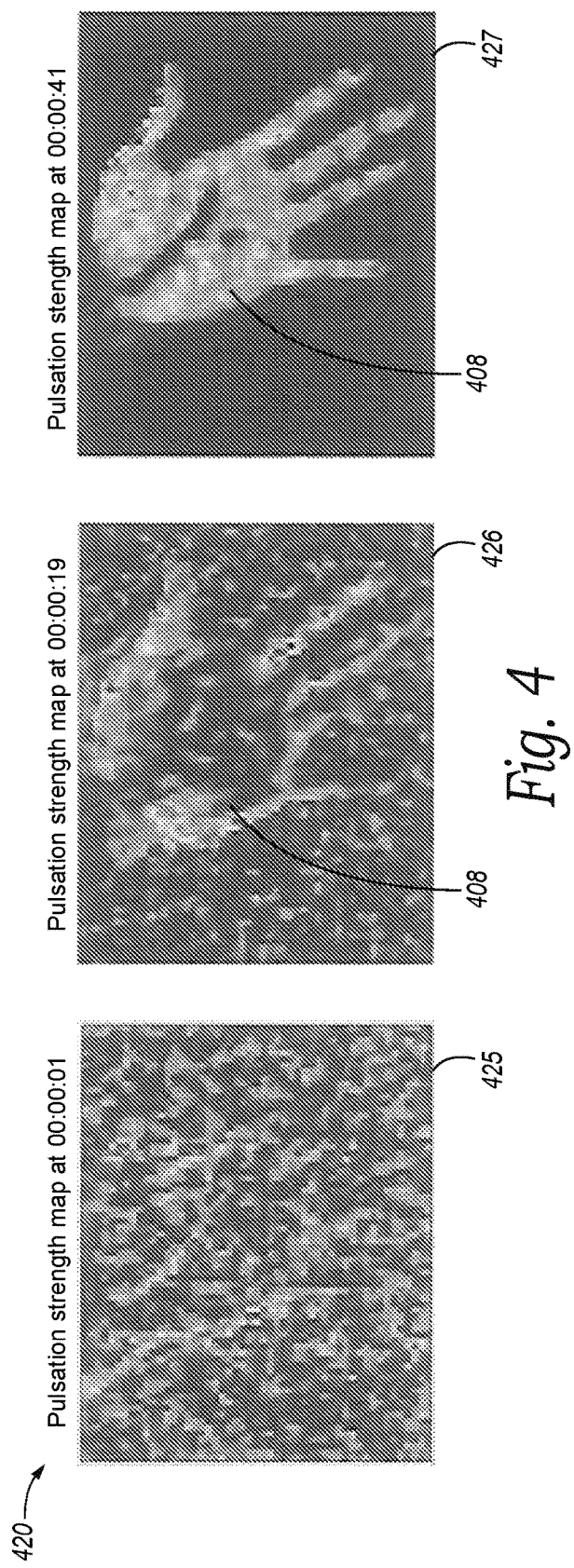
FIG. 4 is a sequence of pulsation strength images generated from RGB images captured using an image capture device of a video-based patient monitoring system according to various embodiments described herein.

In some embodiments, the video-based patient monitoring system can be configured to generate an indication of the strength of one or more physiological parameters within the field of view of the image capture device. For example, FIG. 4 is a sequence 420 of pulsation strength images 425-427 generated from RGB images captured using an image capture device (e.g., the camera 114 and/or 115 shown in FIG. 1 and/or the image capture device 285 shown in FIG. 2) of the video-based patient monitoring system. In particular, the sequence 420 of the pulsation strength images 425-427 illustrates reperfusion in a hand 408 of a patient over approximately 40 seconds. In some embodiments, the system can generate the pulsation strength images 425-427 by directing the image capture device toward a region of the patient (e.g., the patient's hand 408), capturing a sequence of standard RGB images as a video-photoplethysmogram signal, generating pulsation information in accordance with the discussion above, and averaging the pulsation information (e.g., the amplitudes and/or other measures of strength of the pulsation signals) over multiple RGB images and/or multiple heart beats.

The pulsation strength image 425, for example, corresponds to an RGB image captured when blood flow to the hand 408 of the patient is cut off (e.g., via a blood pressure cuff). As shown, little to no pulsation strength information is available in the pulsation strength image 425 because little to no underlying pulsation information is available (as there is little to no blood flow to the hand 408). As a result, the hand 408 is indistinguishable from the background of the pulsation strength image 425, and the colors depicted in the pulsation strength image 425 can largely be attributable to noise detected from the environment.

A pulsation strength image similar to the pulsation strength image 425 can also be generated when not enough underlying pulsation information is available. For example, a similar pulsation strength image can be generated when this feature of the video-based patient monitoring system is first activated, when a region of the patient visible in the field of view of the image capture device changes position within the field of view, and/or when the image capture device is moved.

In contrast, as blood begins to flow into the hand 408 and/or as underlying pulsation information becomes available, the system can generate pulsation strength information by averaging the pulsation information over multiple images and/or heart beats. For example, the hand 408 in the pulsation strength images 426 and 427 becomes distinguishable from the backgrounds of the pulsation strength images 426 and 427 as blood flow is restored to the hand 408 and as an increasing amount of underlying pulsation information becomes available. In this manner, the video-based patient monitoring system can depict pulsation strength information of the hand 408 to a clinician in the pulsation strength images 425-427. Although the sequence 420 of images illustrated in FIG. 4 depicts pulsation strength across the field of view of the image capture device, the video-based patient monitoring system can be configured to generate an indication of the strength of one or more other physiological parameters (e.g., perfusion index, oxygen saturation, respiratory rate, heart rate, etc.) in addition to or in lieu of pulsation strength.

Figure 5:
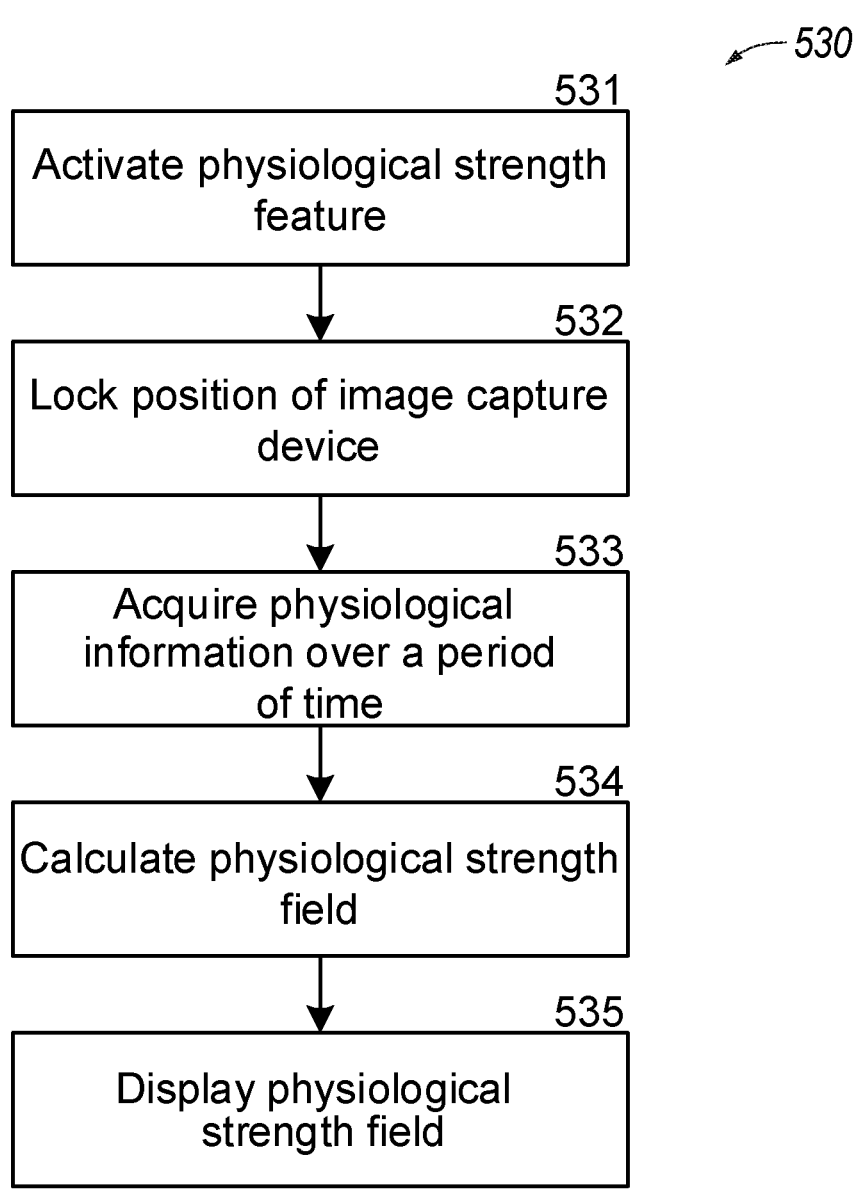
FIG. 5 is a flowchart of a method for generating and displaying a physiological strength field data across a field of view of an image capture device according to various embodiments described herein.

FIG. 5 is a flowchart of a method 530 for generating and displaying a physiological strength field across a field of view of an image capture according to various embodiments described herein. All or a subset of the steps of the method 530 can be executed by various components of a video-based patient monitoring system and/or an operator of the system (e.g., a clinician). For example, all or a subset of the steps of the method 530 can be executed by (i) components of the video-based patient monitoring system 100 shown in FIG. 1 and/or (ii) components of the video-based patient monitoring system 200 shown in FIG. 2.

The method 530 can begin at block 531 by activating the physiological strength field feature. In some embodiments, the method 530 can activate the physiological strength field feature via a set feature option of the video-based patient monitoring system. For example, a clinician can enable the physiological strength field feature by (i) actuating a hardware button or switch on the system, (ii) pressing a corresponding software button option (e.g., on a touchscreen display of the system), and/or (iii) otherwise instructing (e.g., via voice command) the system to enable the physiological strength field feature. In these and other embodiments, the method 530 can automatically activate the physiological strength field feature. For example, the method 530 can activate the physiological strength field feature (i) when the system is powered on and/or (ii) when the image capture device or a region of the patient within the field of view of the image capture device is stationary (e.g., for a predetermined amount of time).

At block 532, the method 530 can lock the position of the image capture device. In some embodiments, the method 530 can lock the position of the image capture device when the method 530 enables the physiological strength field feature (at block 531). In these and other embodiments, the method 530 can lock the position of the image capture device after the physiological strength field feature is enabled and in response to instructions received from the clinician (e.g., via a voice command or other action) and/or the system.

Figure 6A:
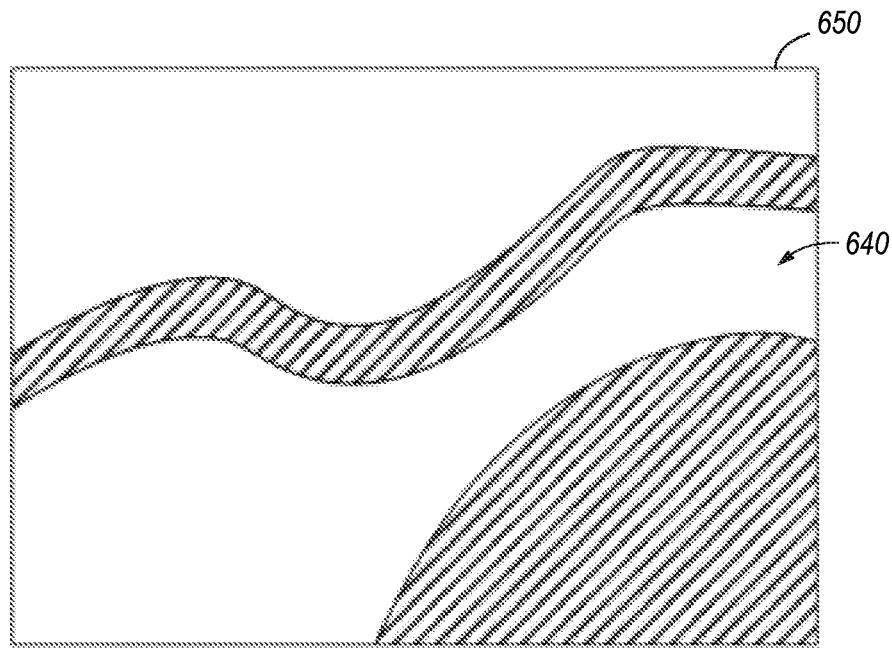
FIGS. 6A and 6B are schematic views of a region of interest (ROI) within a field of view of an image capture device according to various embodiments described herein.

FIG. 6A is a schematic view of an example ROI 640 within a field of view 650 of an image capture device of the video-based patient monitoring system. Using the embodiment illustrated in FIG. 6A as an example, the method 530 (FIG. 5), in some embodiments, can be configured to lock the image capture device in position to hold the ROI 640 stationary within the field of view 650 for a predetermined amount of time (e.g., 10 seconds). For example, the predetermined amount of time can be a period of time sufficient to acquire enough spatial information of one or more physiological parameters of the ROI 640 to generate a robust aggregated physiological strength field view, as discussed in greater detail below with respect to block 533-535 of the method 530. In these and other embodiments, the method 530 can be configured to lock the image capture device in position to hold the ROI 640 within the field of view 650 until a certain number of events have occurred. For example, the method 530 can be configured to lock the image capture device in position until the method 530 determines a certain number of cardiac pulses (e.g., 10 cardiac pulses) and/or a certain number of respiratory cycles (e.g., 3-5 respiratory cycles) have occurred. In these and still other embodiments, the method 530 can lock the image capture device in position for another amount of time (e.g., an amount of time defined within a voice command or other input received from the clinician, an amount of time corresponding to a particular surgical operation, an amount of time corresponding to a particular region of interest, etc.). In some embodiments, the video-based patient monitoring system and/or the image capture device(s) can include an on-board stabilization element that is configured to keep the cameras (e.g., the cameras 114 and/or 115) of the patient monitoring system and/or the image capture device(s) still spatially.

At block 533, the method 530 can acquire physiological information over a period of time. Examples of physiological parameters that the method 530 can acquire include pulsation, perfusion index, oxygen saturation, respiratory rate, and/or heart rate, among others (as described in more detail in co-pending application Ser. Nos. 15/432,057 and 15/432,063). In some embodiments, the method can acquire physiological information over a period of time equivalent to the amount of time the method 530 locks the position of the image capture device (at block 532). In these and other embodiments, the method can acquire physiological information over a period of time greater or lesser than the amount of time the method 530 locks the position of the image capture device. For example, if the position of the image capture device remains unchanged after the method 530 locks the position of the image capture device for an amount of time (at block 532), the method 530 can continue to acquire physiological information (e.g., until the position of the image capture device is changed). In a preferred embodiment, the method 530 can acquire physiological information over a period of time sufficient to acquire enough spatial information of one or more physiological parameters of the ROI 640 (FIG. 6A) to generate a robust aggregated physiological strength field view, as described in greater detail below with respect to blocks 534-535 of the method 530.

Figure 7:
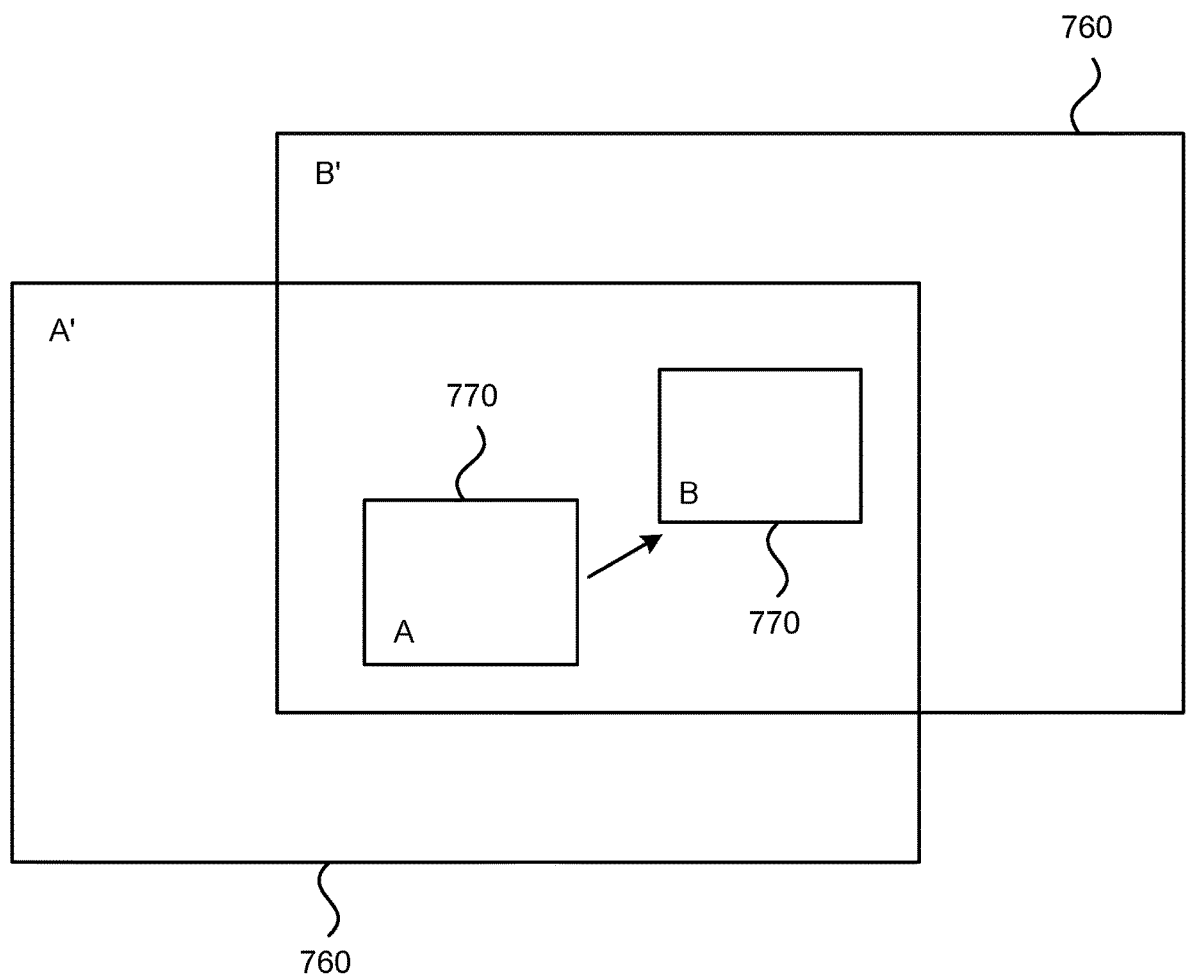
FIG. 7 is a diagram illustrating whole field views and active views of an image capture device according to various embodiments described herein.

In some embodiments, the method 530 can acquire physiological information across all or a subset of the field of view 650 (FIG. 6A) of the image capture device. For example, FIG. 7 is a diagram illustrating a whole field of view 760 of an image capture device at different locations A' and B' and an active field of view 770 of an image capture device at different locations A and B according to various embodiments described herein. The field of view 650 (FIG. 6A) in some embodiments can be a whole field of view equivalent to the whole field of view 760 shown in FIG. 7. In these embodiments, the method 530 can be configured to acquire physiological information across the entirety of the whole field of view 650 and/or 760. In these and other embodiments, the method 530 can be configured to acquire physiological information across a subset of the whole field of view 650 and/or 760. For example, the method 530 can be configured to acquire physiological information across only the active field of view 770 shown within the whole field of view 760 in FIG. 7. In some embodiments, the active field of view 770 can correspond to a subset of the whole field of view 760 and/or can correspond with a region of interest (e.g., ROI 640 shown in FIG. 6A) of a patient. In these and other embodiments, the method 530 can define the active field of view 770 within the whole field of view 650 and/or 760. For example, a clinician can define the active field of view 770 as an input into the system. Additionally, or alternatively, the video-based patient monitoring system can define the active field of view 770 (e.g., by setting the active field of view 770 equivalent to an ROI 640 (FIG. 6A) identified within the whole fields of view 650 and/or 760). Although the active field of view 770 is illustrated having a generally rectangular shape, the active field of view 770 in other embodiments can have a different shape (e.g., the shape of the identified ROI 640).

At block 534, the method 530 can calculate a physiological strength field of one or more physiological parameters of the ROI 640 (FIG. 6A). In some embodiments, the method 530 can calculate a physiological strength field of one or more physiological parameters in accordance with the discussion above with respect to FIGS. 3 and 4. Using pulsation as an example, the method 530 can generate pulsation information pertaining to the ROI 640 from a video-photoplethysmogram signal (e.g., by computing subtle color changes in pixels of RGB images) acquired by the method 530 of the ROI 640 at block 533. This can provide an indication of each pulsation at each site in the ROI 640 in real time. The method 530 can then average the pulsation information (e.g., the amplitudes and/or other measures of strength of the pulsation signals) across multiple RGB images and/or across multiple events (e.g., cardiac pulses, respiratory cycles, etc.) in order to produce a robust estimate of the pulsation strength across the ROI 640. This can provide an indication of perfusion to each site in the ROI 640 over a period of time rather than an instantaneous indication of pulsation at each site, which in turn can help to identify sites within the ROI 640 where blood flow is weak and/or non-existent.

In some embodiments, the method 530 can calculate a physiological strength field across only the active field of view 650 and/or 770 (FIGS. 6A and 7). In other embodiments, the method 530 can calculate a physiological strength field across a subset of the whole field of view 650 and/or 760 shown in FIGS. 6A and 7 (e.g., a subset corresponding to an identified ROI 640 within the whole fields of view 650 and/or 760). In still other embodiments, the methods 530 can calculate a physiological strength field across the entirety of the whole field of view 650 and/or 760.

Figure 6B:
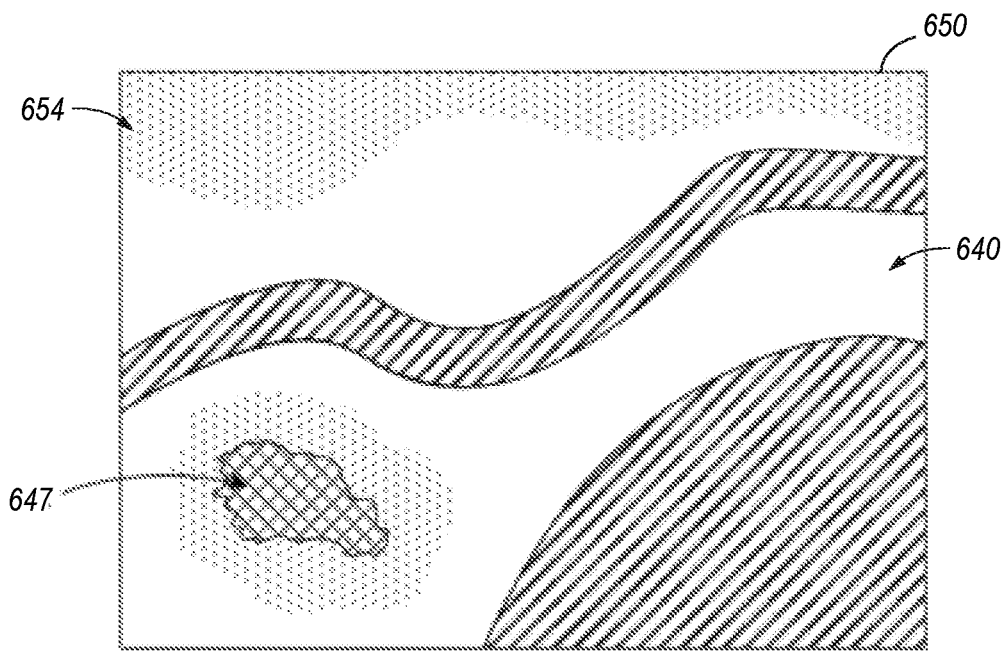

At block 535, the method 530 can display the physiological strength field. In some embodiments, the method 530 can superimpose the physiological strength field on the image of the ROI 640 within the field of view 650 of the image capture device. For example, FIG. 6B is a schematic view of the ROI 640 within the field of view 650 shown in FIG. 6A having a physiological strength field 654 superimposed onto the original image (e.g., onto the entirety of the field of view 650 and/or onto only the ROI 640). In these and other embodiments, the method 530 can (e.g., temporarily) replace the image of the ROI 640 within the field of view 650 of the image capture device with a generated physiological strength field image. The physiological strength field 654 can be colored and/or shaded according to the strength or value of the physiological field.

In some embodiments, the method 530 can be configured to display to a clinician all or a subset of the calculated physiological strength field across the whole field of view 650 and/or 760 and/or across the active field of view 650 and/or 770. In these embodiments, the whole field of view 650 and/or 760 can correspond to an entire area visible to the image capture device and/or the active field of views 650 and/or 770 can correspond to a subset of the entire area that is displayed to a clinician. For example, in embodiments where the field of view 650 (FIGS. 6A and 6B) is equivalent to the whole field of view 760 (FIG. 7) and the method 530 calculates a physiological strength field across the entirety of the whole field of view 760 (at block 534), the method 530 can be configured to display to the clinician only the portion(s) of the calculated physiological strength field corresponding to the active field of view 770. This allows the method 530 to instantly and/or automatically display the physiological strength field within the active field of view 770 when a clinician moves the image capture device (and thereby moves the whole field of view 760 and the active field of view 770) to a new position without first having to wait for the method 530 to calculate the physiological strength field (at blocks 531-534) at the new location.

Using the embodiment illustrated in FIG. 7 as an example, the method 530 can acquire physiological information (at block 533) and can calculate a physiological strength field (at block 534) across a whole field of view 760 of an image capture device while the whole field of view 760 is at location A'. Although the method 530 has acquired physiological information and calculated the physiological strength field across the entire whole field of view 760, the method 530 can display only a portion of the physiological information and/or of the physiological strength field that corresponds to the active field of view 770 at location A (e.g., only the portion of the physiological information and/or of the physiological strength field at the center of the whole field of view 760 at location A'). Because the method 530 has acquired physiological information and/or has calculated a physiological strength field across the entirety of the whole field of view 760, the method 530 can instantly and/or automatically display a portion of the physiological information and/or of the physiological strength field at different locations within the whole field of view 760 when the image capture device is moved (e.g., shifted, changed, etc.). For example, a clinician can subsequently move the image capture device such that the active field of view 770 shifts (e.g., moves, changes, etc.) from location A to location B. Because the active field of view at location B is still within the whole field of view 760 at location A' (i.e., because the method 530 has already acquired physiological information and/or has already calculated a physiological strength field at location B), the method 530 can instantly and/or automatically display the portion of the physiological information and/or of the physiological strength field corresponding to the active field of view 770 at location B. As a result, the method 530 (e.g., the clinician) is not required to wait for the method 530 to acquire the physiological information and/or to calculate the physiological strength field at this new location B before the method 530 can display the physiological information and/or the physiological strength field at this new location B.

In some embodiments, when the image capture device and/or the active field of view 770 is shifted (e.g., moved, changed, etc.), the method 530 can be configured to (e.g., automatically and/or in response to received instructions) shift (e.g., change, move, etc.) the whole field of view 760. For example, when the image capture device is shifted such that the active field of view 770 is shifted from location A to location B, the method 530 can be configured to shift the whole field of view 760 from location A' to location B'. In these embodiments, the method 530 can be configured to (e.g., automatically and/or in response to received instructions) acquire physiological information and/or to calculate a physiological strength field across the whole field of view 760 at the new location B'. Thus, when a clinician subsequently shifts the image capture device such that the active field of view 770 is shifted to a new location within the whole field of view 760 at location B', the method 530 can instantly and/or automatically display an updated portion of the physiological information and/or of the physiological strength field corresponding to the active field of view 770 at the new location. Although the active field of view 770 is illustrated at the center of the whole field of view 760, the active field of view 770 in other embodiments can be positioned at other locations within the whole field of view 760 of the image capture device.

As discussed above, a clinician display in some embodiments can be virtual, augmented, and/or mixed reality goggles. In these embodiments, the active field of view 770 can be a portion of the whole field of view 760 displayed on the goggles. Thus, as a clinician moves and the position and/or orientation of the goggles changes, the method 530 can instantly and/or automatically display physiological information and/or physiological strength information corresponding to the active field of view 770 at the new position.

In this manner, the method 530 can provide a robust estimate of the physiological strength field across an ROI 640 even despite the frequently changing location of the fields of view 650 of the image capture device during surgery. As a result, a clinician can quickly identify potential problem sites 647 (FIG. 6B) in the ROI 640 from the visual indication of the physiological strength field across the ROI 640. For example, the problem site 647 shown in FIG. 6B within the ROI 640 can represent a region of low perfusion if the depicted physiological strength field were a perfusion index strength field. Alternatively, the problem site 647 within the ROI 640 can represent a region of hypoxia if the depicted physiological strength field were an oxygen saturation strength field.

Although the steps of the method 530 are discussed and illustrated in a particular order, the method 530 in FIG. 5 is not so limited. In other embodiments, the method 530 can be performed in a different order. In these and other embodiments, any of the steps of the method 530 can be performed before, during, and/or after any of the other steps of the method 530. Moreover, a person of ordinary skill in the relevant art will readily recognize that the illustrated method can be altered and still remain within these and other embodiments of the present technology. For example, one or more steps of the method 530 illustrated in FIG. 5 can be omitted and/or repeated in some embodiments.

As discussed above, video-based patient monitoring systems configured in accordance with various embodiments of the present technology can be configured to indicate and/or identify potential problem sites within a region of interest monitored by an image capture device of the systems. For example, in some embodiments, the systems can be configured to indicate and/or identify regions of poor perfusion that may be susceptible to hypoxia. In particular, the systems can monitor a region of interest before and after blood supply is cut off from (or returned to) the region of interest. Cutting off or returning blood supply to a region should result in a noticeable change in light intensity and/or color in the region, such as disappearance or reappearance of pulsatile changes in light and/or color. Parts of the region of interest that do not markedly change in light intensity and/or color may be identified as abnormally low perfusion regions.

Figure 8:
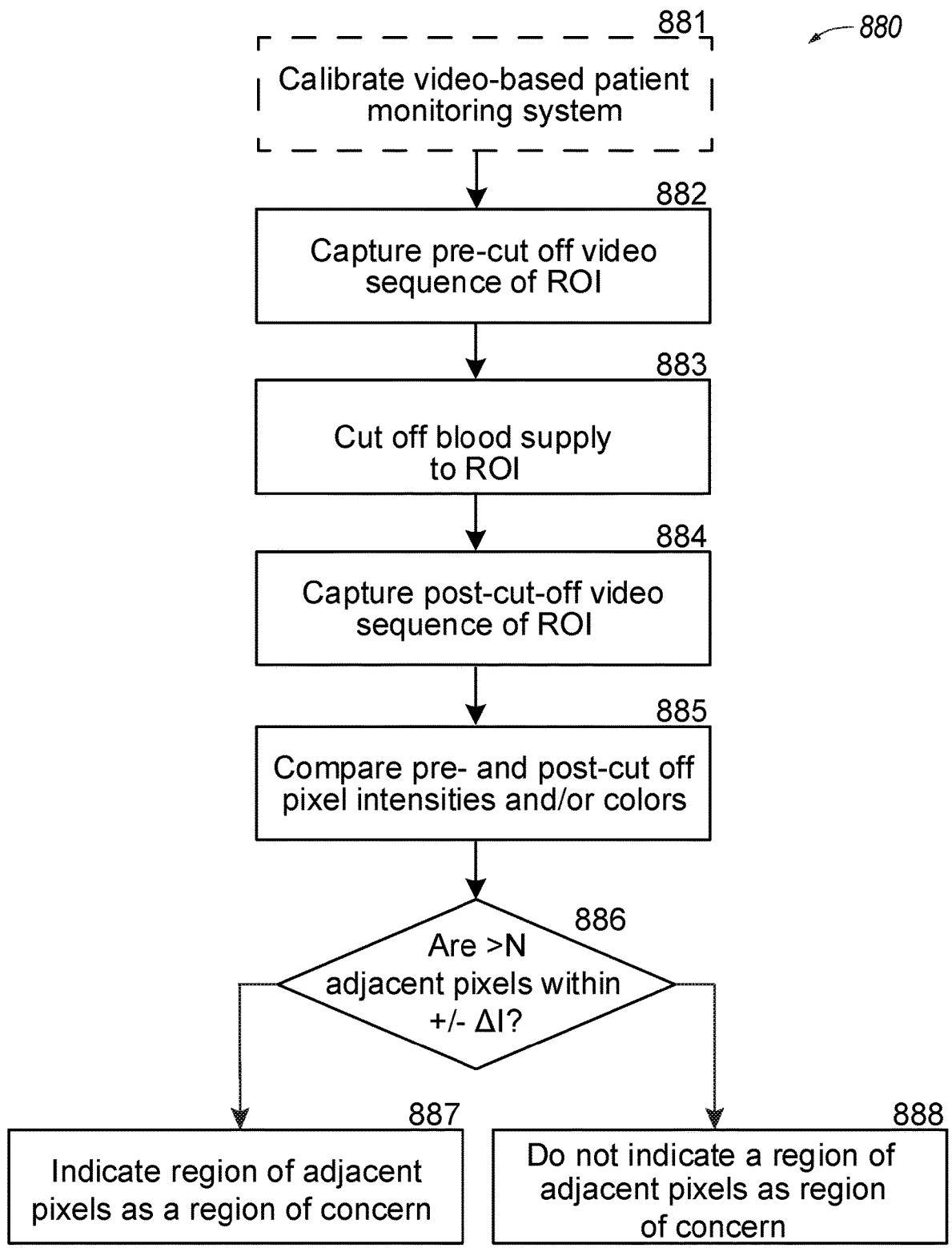
FIG. 8 is a flowchart of a method for determining low perfusion regions in a region of interest according to various embodiments described herein.

FIG. 8 is a flowchart of a method 880 for determining low perfusion regions in a region of interest according to various embodiments described herein. All or a subset of the steps of the method 880 can be executed by various components of a video-based patient monitoring system and/or an operator of the system (e.g., a clinician). For example, all or a subset of the steps of the method 880 can be executed by (i) components of the video-based patient monitoring system 100 shown in FIG. 1 and/or (ii) components of the video-based patient monitoring system 200 shown in FIG. 2.

Figure 9A:
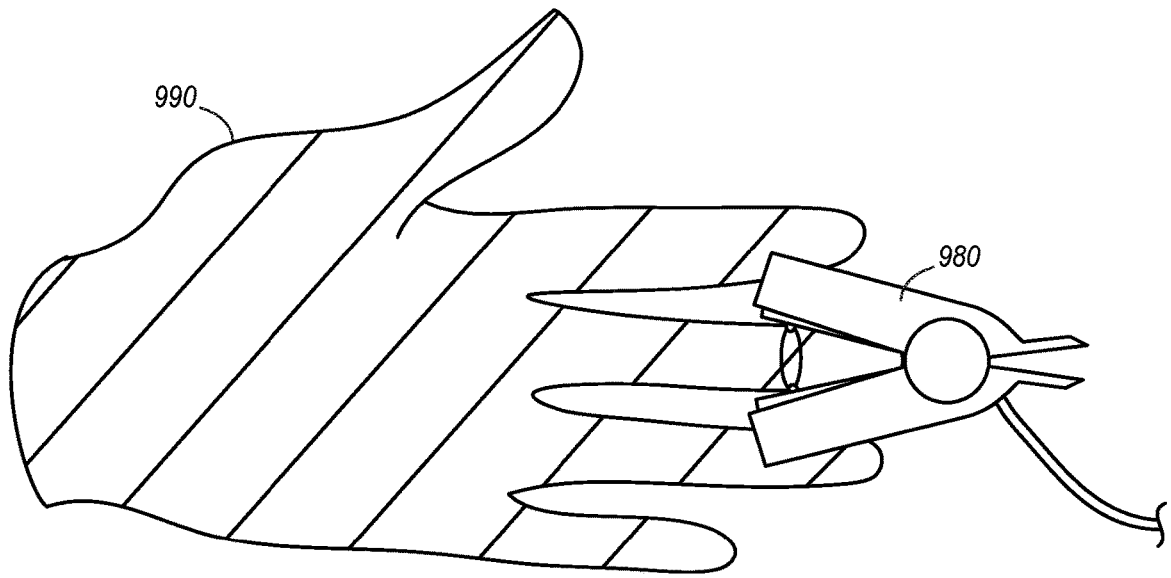
FIGS. 9A and 9B are schematic diagrams of a perfusion region of interest according to various embodiments described herein.

FIG. 9A is a schematic diagram of a perfusion ROI 990. Using the embodiment illustrated in FIG. 9A as an example, the method 880 illustrated in FIG. 8 can begin at block 881 to calibrate the video-based patient monitoring system. In some embodiments, the method 880 can calibrate the video-based patient monitoring system using a pulse oximeter 980 (FIG. 9A). In particular, the method 880 can attach the pulse oximeter 980 to the ROI 990 and can take a point measure of the ROI 990 using the pulse oximeter 980 to calculate a perfusion index that can be used to calibrate the video-based patient monitoring system to the ROI 990 (e.g., across the whole and/or active field of view of the image capture device). Calibrating the video-based patient monitoring system to the ROI 990 can allow the method 880 to calculate an absolute value of perfusion and/or another measure of perfusion at the surface of the ROI 990, as described in greater detail below with respect to blocks 884 and 885 of the method 880. In some embodiments, the method 880 can proceed to block 882 after calibrating the video-based patient monitoring system.

Alternatively, the method 880 in some embodiments can begin at block 882. For example, the method 880 can begin at block 882 if the method 880 has previously calibrated the video-based patient monitoring system to the ROI 990 (e.g., in a previous iteration of the method 880). In other embodiments, the method 880 can begin at block 882 without calibrating the video-based patient monitoring system. For example, the method 880 in some embodiments can calculate a relative change in light intensity and/or color at the surface of the ROI 990, as described in greater detail below with respect to block 884-885 of the method 880, regardless of whether the video-based patient monitoring system has been calibrated to the ROI 990.

At block 882, the method 880 can capture a video sequence of the ROI 990 before blood flow to the region is cut off (this can be referred to as a pre-cut off video sequence). In some embodiments, the method 880 can capture a pre-cut off sequence of RGB images of the ROI 990 in accordance with the discussion above with respect to FIGS. 3-7. For example, the method 880 can capture a pre-cut off sequence of RGB images as a video-photoplethysmogram signal using an RGB camera (e.g., the RGB camera 114 shown in FIG. 1) of the video-based patient monitoring system.

At block 883, the method 880 can cut off blood supply to the ROI 990. In some embodiments, the method 880 can cut off blood supply to the ROI 990 automatically after capturing a pre-cut off video sequence of the ROI 990 at block 882. In other embodiments, the method 880 can wait to cut off blood supply to the ROI 990 until instructed to do so (e.g., via a voice command and/or an input into the video-based patient monitoring system).

In some embodiments, the method 880 can cut off blood supply to the ROI 990 using a blood pressure cuff, one or more tourniquets, and/or by pressing on the ROI 990 (e.g., the skin at the ROI 990). For example, a clinician can manually cut off blood supply to the ROI 990 using the blood pressure cuff, the one or more tourniquets, and/or by pressing on (e.g., squeezing) the ROI 990. In these embodiments, the clinician can inform the video-based patient monitoring system whether blood supply has been cut off to the ROI 990. In these and other embodiments, the blood pressure cuff can be coupled to the image capture device of the video-based patient monitoring system. In these embodiments, the before and after blood supply cut-off periods can be determined automatically. For example, the method 880 can instruct the blood pressure cuff to cut off blood supply to the ROI 990. Because the blood pressure cuff is coupled to the image capture device of the video-based patient monitoring system, the image capture device can be aware of when blood supply is cut off to the ROI 990 and/or can automatically begin capturing pre- and/or post-cut off video sequences of the ROI 990 (at blocks 882 and/or 884).

At block 884, the method 880 can capture a post-cut off video sequence of the ROI 990 after the mechanism to cut off blood supply is discontinued. In some embodiments, the method 880 can capture a post-cut off sequence of RGB images of the ROI 990 in accordance with the discussion above with respect to FIGS. 3-7. For example, the method 880 can capture a post-cut off sequence of RGB images using an RGB camera (e.g., the RGB camera 114 shown in FIG. 1) of the video-based patient monitoring system as a video-photoplethysmogram signal.

At block 885, the method 880 can compare the pre-cut off video sequence to the post-cut off video sequence. In some embodiments, the method 880 can compare the relative change in pixel intensities (e.g., light intensity) and/or color between the pixels in the pre-cut off video sequence and the corresponding pixels in the post-cut off video sequence. In these and other embodiments, the method 880 can compare the absolute values of perfusion index and other measure of perfusion between the pixels in the pre-cut off video sequence and the corresponding pixels in the post-cut off video sequence. For example, the method 880 can compare pixel intensities and/or colors in one RGB image of the pre-cut off video sequence to the pixel intensities and/or colors in (e.g., a corresponding) one of the RGB images of the post-cut off video sequence. In these and other embodiments, the method 880 can compare average pixel intensities and/or colors in the pre-cut off video sequence to corresponding average pixel intensities and/or colors in the post-cut off video sequence.

As discussed above, parts of the ROI 990 that do not markedly change in light intensity and/or color may be identified to a clinician as abnormally low perfusion regions because cutting off blood supply to the ROI 990 should result in a significant change in the video-perfusion measure of all parts of the ROI 990. Thus, at block 886, the method 880 can determine whether a threshold number (e.g., two or more) of adjacent pixels in parts of the ROI 990 maintain light intensity and/or color levels within a specified range (e.g., 1%, 2%, 5%, 10%, etc.) between the pre-cut off video sequence and the post-cut off video sequence. For example, the method 880 can determine a part of the ROI 990 is an abnormally low perfusion region if adjacent pixels in that region maintain light intensity and/or color levels within a specified range of light intensity and/or color levels in the pre-cut off and post-cut off video sequences. The specified range of light intensity and/or color levels can be tailored to an individual patient and/or surgical procedure (e.g., to different skin colors, to different organ colors, etc.). If the method 880 determines that a total number of adjacent pixels in a part of the ROI 990 greater than the threshold number maintained light intensity and/or color levels within the specified range between the pre-cut off video sequence and the post-cut off video sequence, the method 880 can proceed to block 887 to indicate the part as a region of concern. Otherwise, the method 880 can proceed to block 888 to not indicate the part as a region of concern.

In these and other embodiments, the method 880 can determine that a part of the ROI 990 is an abnormally low perfusion region if a gradient change in light intensity and/or color level is sufficiently different in one group of pixels compared to another group of pixels. For example, if the method 880 determines that a gradient change in light intensities and/or color levels across adjacent pixels in a first group of pixels differs from the gradient change in a second group of pixels by more than a specified threshold value (e.g., 50%), this can indicate that one of those two groups of pixels is changing while the other is not. For example, if the gradient in the first group of pixels is high, and the gradient in the second is low, this can identify the first group of pixels as a well-perfused region (losing perfusion when the blood supply is cut off) and the second group of pixels as a poorly perfused region (not experiencing a change when the blood supply is cut off). The specified threshold value can be tailored to an individual patient and/or procedure (e.g., to different skin colors, to different organ colors, etc.). If the method 880 determines that the gradient change in light intensity and/or color level is greater than the specified threshold, the method 880 can proceed to block 887 to indicate a corresponding group of adjacent pixels as a region of concern. Otherwise, the method 880 can proceed to block 888 to not indicate the part as a region of concern.

Figure 9B:
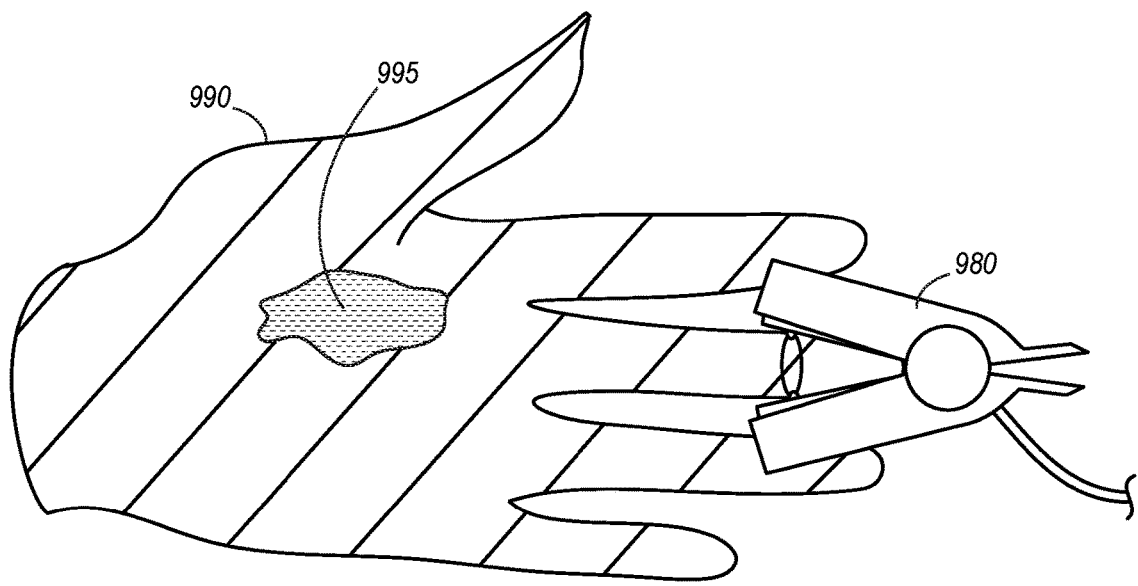

FIG. 9B is a schematic diagram of a region of concern 995 within the perfusion ROI 990 shown in FIG. 9A. In some embodiments, the region of concern 995 can correspond to a part of the ROI 990 exhibiting signs of abnormally low perfusion. Using the embodiment illustrated in FIG. 9B as an example, the method 880 can indicate a region of concern 995 on a displayed video image at block 887. In some embodiments, the method 880 can indicate the region of concern 995 by highlighting the corresponding part of the ROI 990 on the video image (e.g., displayed to a clinician). In these and other embodiments, the method 880 can indicate the region of concern 995 by activating an audio and/or visual alarm to, for example, alert a clinician of the region of concern 995. Although the region of concern 995 corresponds to only a part of the ROI 990 in the embodiment illustrated in FIG. 9B, the method 880 in other embodiments can indicate the entire ROI 990 as a region of concern.

At block 888, the method 880 does not indicate a region of concern within the ROI 990. For example, the method 880 does not indicate a region of concern within the ROI 990 where the method 880 (at block 886) has determined there is not a number of adjacent pixels (that maintained light intensities and/or color levels within the specified range between the pre-cut off video sequence and the post-cut off video sequence) greater than the threshold number.

In some embodiments, several iterations of the method 880 can be executed. For example, several iterations of the method 880 can be executed to determine and/or monitor the progress of the ROI 990 and/or of a region of concern over time (e.g., during the progression of a disease state, during reperfusion of a ROI, and/or during recovery). In these and other embodiments, the method 880 can be configured to activate an audio and/or visual alarm if a deterioration is detected. For example, if the perfusion index within the ROI 990 and/or within the region of concern 995 falls below a specified threshold, such as 50 percent reduction in the perfusion index compared to the normal state or a known acceptable norm, the method 880 can activate the audio and/or visual alarm. In some embodiments, a threshold value may be used in addition to or in lieu of a relative percentage reduction. For example, an alarm may sound if the perfusion index falls below 1%, 0.1%, 0.01%, etc. The threshold value can be dependent on an individual patient and/or his/her health status. For example, a patient may have low perfusion issues, and the normal range of perfusion index may not be applicable to them. As such, the relative percentage reduction and/or the threshold value can be specified and/or tailored to a specific patient. Therefore, all or a subset of the steps of the method 880 can be useful in an operating room, an intensive care unit, within a home environment, and/or in a number of use cases (e.g., reperfusion, hypoxia, deteriorating patient conditions, etc.).

Although the steps of the method 880 are discussed and illustrated in a particular order, the method 880 in FIG. 8 is not so limited. In other embodiments, the method 880 can be performed in a different order. For example, the order of block 882-884 of the method 880 can be reversed in some embodiments. In these and other embodiments, any of the steps of the method 880 can be performed before, during, and/or after any of the other steps of the method 880. Moreover, a person of ordinary skill in the relevant art will readily recognize that the illustrated method can be altered and still remain within these and other embodiments of the present technology. For example, one or more steps of the method 880 illustrated in FIG. 8 can be omitted and/or repeated in some embodiments.

Figure 10:
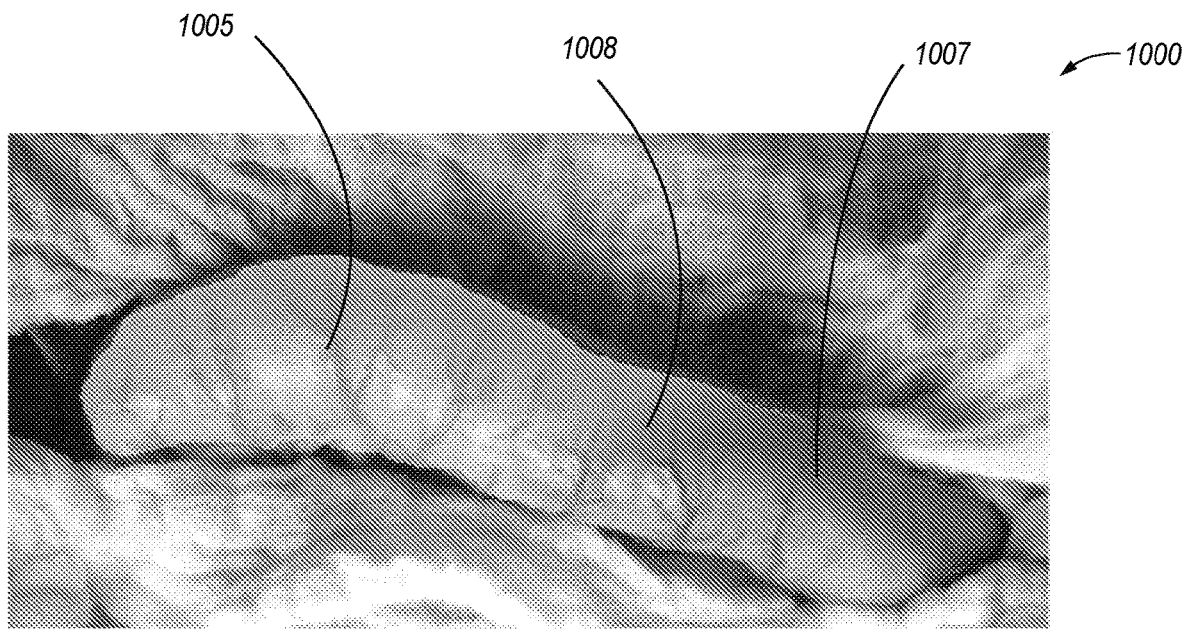
FIG. 10 is an image of patient region of interest injected with indocyanine green (ICG) dye and captured using an image capture device according to various embodiments described herein.

FIG. 10 is an image 1000 of ROI 1007 (e.g., an organ) injected with ICG dye 1005 and captured using an image capture device of a video-based patient monitoring system according to various embodiments described herein. For example, the image 1000 can be captured by (i) the cameras 114 and/or 115 of the video-based patient monitoring system 100 illustrated in FIG. 1 and/or (ii) by the image capture device(s) 285 of the video-based patient monitoring system 200 illustrated in FIG. 2. The ROI 1007 illustrated in the image 1000 is a colon within a patient. As discussed above, blood flow in the ROI 1007 can be monitored by injecting the ICG dye 1005 into the patient and using a tuned infrared light source and an IR camera (or an RGB camera with an IR filter) to visually track the ICG dye 1005. In particular, the ICG dye 1005 can be injected upstream from the ROI 1007, and blood can transport the ICG dye 1005 to and/or through ROI 1007.

As shown in FIG. 10, the part of the ROI 1007 illustrated in the left half of the image 1000 is illuminated with the ICG dye 1005. Presence of the ICG dye 1005 in this part of the ROI 1007 indicates that the part is receiving blood flow from the site at which the ICG dye 1005 was injected (e.g., via an IV or a syringe). In contrast, the part of the ROI 1007 illustrated in the right half of the image 1000 is not illuminated with the ICG dye 1005. The lack of ICG dye 1005 in this part of the ROI 1007 indicates that there is less perfusion, which may indicate an occlusion 1008 between the part of the ROI 1007 on the left and the part of the ROI 1007 on the right that is inhibiting and/or preventing blood flow into the part of the ROI 1007 on the right from the part of the ROI 1007 on the left. In this manner, the video-based patient monitoring system can use the ICG dye 1005 to identify potential sites (e.g., of occlusions 1008) where blood flow has decreased and/or ceased within the ROI 1007 by identifying parts of the ROI 1007 where none of the ICG dye 1005 is present.

As discussed above, there are, however, several limitations to use of the ICG dye 1005 as the sole indication of blood flow within an ROI 1007. Thus, systems, device, and/or methods configured in accordance with embodiments of the present technology are configured to combine RGB-derived pulsation information with ICG-derived information to overcome one or more of the shortcomings outlined above (among others), as described in greater detail below.

Figure 11:
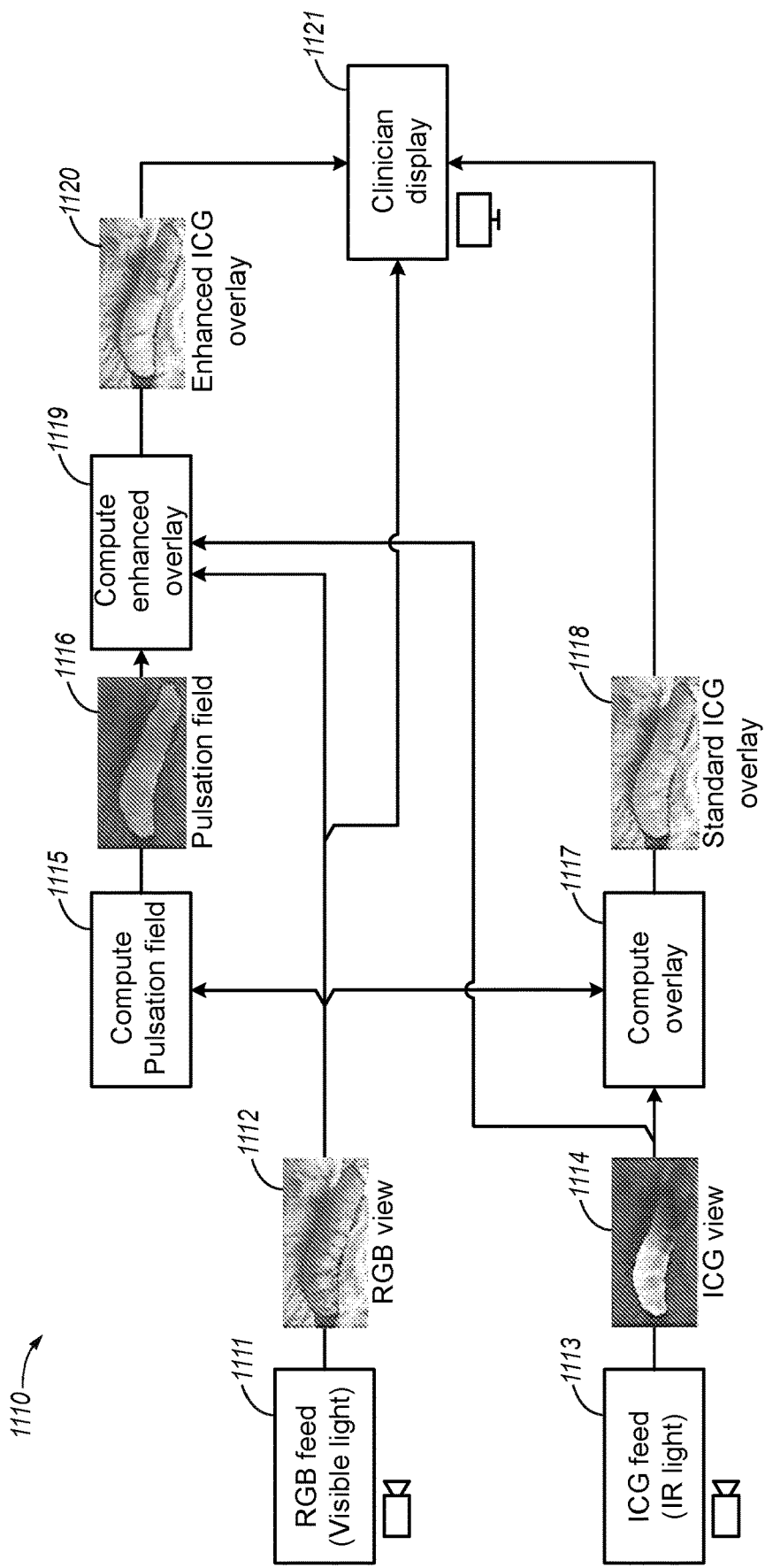
FIG. 11 is a flowchart of a method for obtaining and displaying pulsation and/or blood flow in a region of interest according to various embodiments described herein.

FIG. 11 is a flowchart of a method 1110 for obtaining and displaying pulsation and/or blood flow in a region of interest according to various embodiments described herein. All or a subset of the steps of the method 1110 can be executed by various components of a video-based patient monitoring system and/or an operator of the system (e.g., a clinician). For example, all or a subset of the steps of the method 1110 can be executed by (i) components of the video-based patient monitoring system 100 shown in FIG. 1 and/or (ii) components of the video-based patient monitoring system 200 shown in FIG. 2.

The method 1110 can begin at blocks 1111 and 1112 to capture an RGB video sequence of a region of interest (ROI) to produce an RGB view. In some embodiments, the method 1110 can capture an RGB video sequence using a non-contact detector, such as an image capture device and/or video camera (e.g., the video camera(s) 114 and/or 115 of the non-contact detector 110 shown in FIG. 1 and/or the image capture device(s) 285 shown in FIG. 2). For example, the method 1110 can capture an RGB video sequence of the ROI using a standard or scientific RGB camera.

At blocks 1113 and 1114, the method 1110 can capture an ICG video sequence of the ROI to produce an ICG view. In some embodiments, the method 1110 can capture an ICG video sequence using a non-contact detector, such as an image capture device and/or video camera (e.g., the video camera(s) 114 and/or 115 of the non-contact detector 110 shown in FIG. 1 and/or the image capture device(s) 285 shown in FIG. 2). For example, the method 1110 can capture an ICG video sequence of the ROI using a tuned IR light source and a video camera with an IR filter or using other, more sophisticated lighting methods, such as sequential lighting and background subtraction.

At blocks 1115 and 1116, the method 1110 can compute a pulsation field and/or a pulsation strength field to produce a pulsation field view. In some embodiments, the method 1110 can compute a pulsation field across the field of view of the RGB video sequence in accordance with the discussion above with respect to FIG. 3. For example, the method 1110 can compute a pulsation field from the subtle color changes and/or changes in light intensities in pixels of RGB images in the RGB video sequence to provide an indication of the state of perfusion within the ROI. In these and other embodiments, the method 1110 can compute the pulsation field in real time. In these and still other embodiments, the method 1110 can compute a pulsation strength field across the field of view of the RGB video sequence in accordance with the discussion above with respect to FIGS. 4-7. For example, the method 1110 can compute a pulsation strength field by averaging the (e.g., amplitudes) of the subtle color changes over several RGB images in the RGB video sequence and/or over a period of time to provide an indication of perfusion (perfusion index) within the ROI. In these and still other embodiments, the method 1110 can compute a pulsation field and/or a pulsation strength field using an ICG fluorescent region of the ICG view as a mask to perform the pulsation field and/or pulsation strength field calculations. In this manner, the pulsation signal quality can be improved by removing background noise from the overall computation.

At blocks 1117 and 1118, the method 1110 can compute a standard ICG overlay. In some embodiments, the method 1110 can compute a standard ICG overlay by superimposing the RGB video sequence onto the ICG video sequence. In these and other embodiments, the method 1110 can compute a standard ICG overlay by superimposing the ICG video sequence onto the RGB video sequence. As discussed above, the standard ICG overlay can provide an indication of the parts of a ROI that are receiving blood flow and/or an indication of potential poorly perfused sites within the ROI where blood flow has decreased and/or ceased. The poorly perfused sites may be due to an occlusion or significant vasoconstriction.

At blocks 1119 and 1120, the method 1110 can compute an enhanced ICG overlay. In some embodiments, the method 1110 can compute an enhanced ICG overlay by superimposing and/or blending the pulsation field computed at blocks 1115 and 1116 with the ICG view. This can provide an indication of pulsatile flow within the ROI. In this manner, if blood flow decreases and/or ceases at a site within the ROI, the enhanced ICG overlay can indicate that pulsations have decreased and/or ceased at the site even though ICG dye is still present at the site. The blending method used to combine ICG overlay and pulsation field overlay can be optimized to make these clinical regions visibly highlighted such as by exaggerating the color changes on the graphical screen to the user.

In these and other embodiments, the method 1110 can compute an enhanced ICG overlay by superimposing the pulsation strength field computed at blocks 1115 and 1116 onto the ICG video sequence. In some embodiments, the method 1110 can quantify the state of perfusion within an ROI using the enhanced ICG overlay. For example, in embodiments where (i) blood flow has been cut off to a ROI using a clamp and (ii) ICG dye had been injected into the patient upstream from the ROI but has not yet been introduced into the ROI, the enhanced ICG overlay can quantify the state of perfusion within the ROI as the clamp is released and blood flow is restored to the ROI. The method 1110 will detect ICG dye that is introduced into the ROI via the reperfusion flow, and the enhanced ICG overlay can quantify the state of perfusion within the ROI before the ICG dye causes image saturation within the ROI. In these and other embodiments, the method 1110 can average the amplitude (or another measure of strength of the signal) at a site within the ROI over a period of time (e.g., 3-5 seconds) to compute an indication of perfusion (e.g., a perfusion index) at the site. In this manner, the average strength of the pulsations at a site within the ROI can be assessed as a measure of local perfusion as the clamp is released and blood flow is restored to the ROI.

Figure 12:
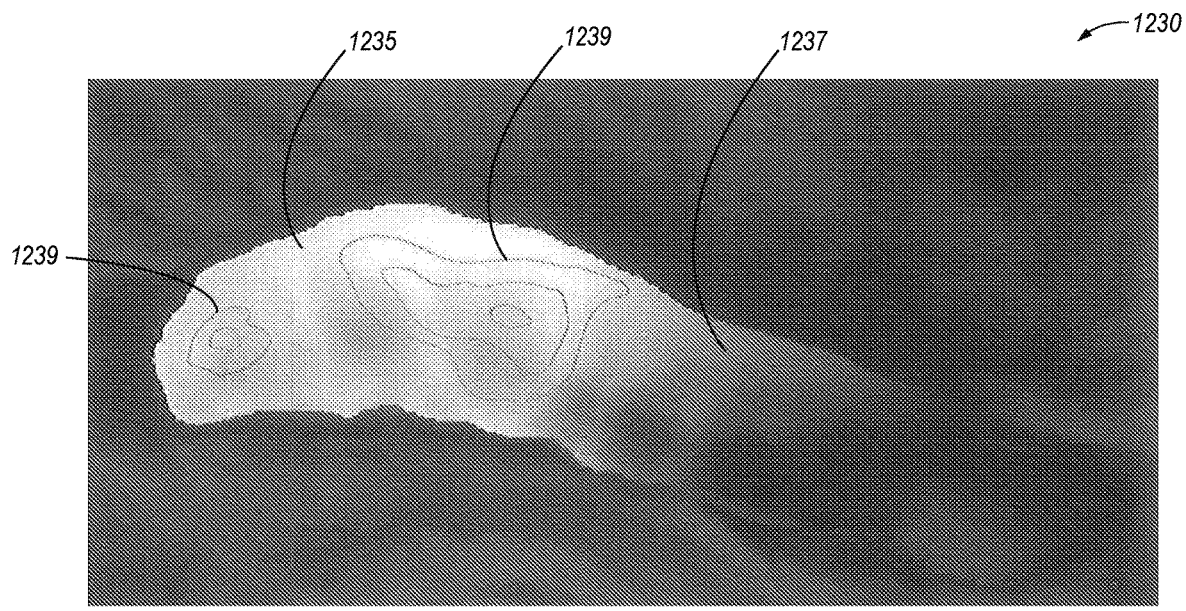
FIG. 12 is a schematic image of a region of interest illustrating pulsation contours plotted on top of an ICG image according to embodiments described herein.
Figure 13:
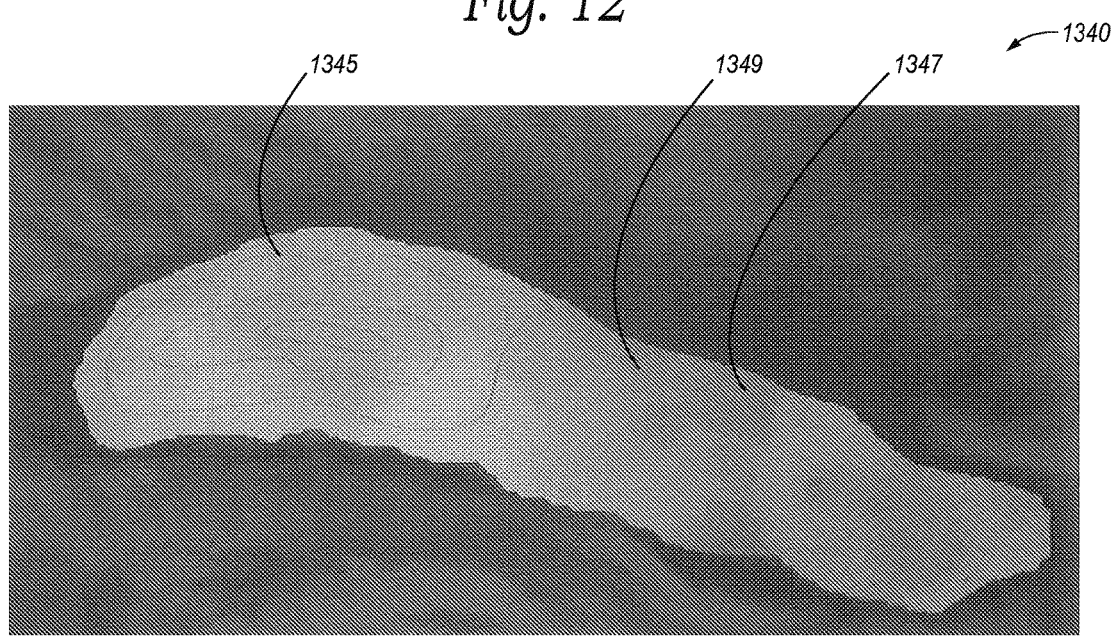
FIG. 13 is a schematic image of a region of interest illustrating ICG contours plotted on top of an RGB-based pulsation image according to embodiments described herein.

In these and still other embodiments, the method 1110 can compute an enhanced ICG overlay with percentage intensity contours derived from the RGB video sequence and/or the ICG video sequence. For example, FIG. 12 is a schematic image 1230 of a region of interest (ROI) 1237 illustrating pulsation contours 1239 plotted on top of the ICG view (produced at block 1114 of the method 1110) showing the ICG dye 1235 according to embodiments described herein. The method 1110 can derive the pulsation contours 1239 from the RGB video sequence by iteratively applying a threshold(s) to the generated pulsation strength field and extracting boundaries from the resulting non-zero regions. In some embodiments, the threshold(s) can be predetermined and/or fixed. In these and other embodiments, the threshold(s) can be relative to a range of pulsation strength values present and/or calculated in the pulsation strength field. For example, the method 1110 can use a pulsation strength value with the largest magnitude in the pulsation strength field to define a 100% pulsation strength value. In these and other embodiments, the method 1110 can generate the pulsation contours 1239 by applying one or more threshold(s) at specific percentages (e.g., 20%, 40%, 60%, 80%, and/or one or more other percentages) of the 100% pulsation strength value to the generated pulsation strength field. As another example, FIG. 13 is a schematic image 1340 of a region of interest (ROI) 1347 illustrating ICG contours 1345 plotted on top of a pulsation field (computed at blocks 1115 and 1116 of the method 1110) according to embodiments described herein. The method 1110 can derive the ICG contours 1345 from the ICG video sequence in a manner similar to how the method 1110 derives the pulsation contours 1239. For example, the method 1110 can derive the ICG contours 1345 by iteratively applying threshold(s) to the generated ICG view and extracting boundaries from the resulting non-zero regions. The threshold values can be predetermined, fixed, and/or relative to the range of ICG intensity values present and/or calculated in the generated ICG view.

At block 1121, the method 1110 can display one or more of the produced and/or computed views on a clinician display. For example, the method 1110 can display the RGB view, the ICG view, the computed pulsation field, the computed pulsation strength field, the standard ICG overlay, and/or the enhanced ICG overlay on the clinician display. In some embodiments, the method 1110 can display one or more of the produced and/or computed views using various hues or colors to distinguish which view is currently displayed on the clinician display. For example, green can be used to indicate the presence of ICG dye within the ICG view, the standard ICG overlay, and/or the enhanced ICG overlay. In some embodiments, various hues of green and/or various colors can be used to indicate that other information (e.g., pulsation and/or pulsation strength) is currently displayed on the clinician display in addition to an indication of the presence of the ICG dye. For example, various hues of blue can be used to indicate pulsation strength. In these and other embodiments, various hues of red and/or yellow can be used to indicate pulsation.

In some embodiments, the clinician display can be virtual, augmented, and/or mixed reality goggles. In these embodiments, a clinician can select a desired view from the one or more of the produced and/or computed views on the goggles. The method 1110 in some embodiments can update (e.g., adjust) a field of view of the desired view displayed on the goggles as the position and/or orientation of the goggles changes (e.g., as the clinician moves and/or looks around).

FIG. 14 is a table 1450 illustrating possible ICG and RGB information combinations and corresponding interpretations according to embodiments described herein. In some embodiments, if the method 1110 displays strong ICG information and strong RGB information at a site within the ROI, the ROI likely has strong blood flow and perfusion at the site. Thus, the tissue at the site is likely viable. In these and other embodiments, if the method 1110 displays strong ICG information but weak or no RGB information at the site within the ROI, blood flow to the site (i) has likely been cut off subsequent to ICG dye injection and/or (ii) is likely very low. Thus, the tissue at the site is likely at risk of hypoxia. In these and still other embodiments, if the method 1110 displays weak or no ICG information but strong RGB information at the site, the ROI likely has strong blood flow and perfusion at the site while the ICG dye has yet to be injected and/or was injected at the wrong site. In these and still other embodiments, if the method 1110 displays weak or no ICG information and weak or no RGB information at the site, the ROI likely does not have blood flow or perfusion at the site. Thus, the tissue at the site is likely at risk of hypoxia.

In some embodiments, the method 1110 can trigger an audio and/or visual alarm (e.g., on the clinician display) to indicate a concerning condition. For example, the method 1110 can trigger an audio and/or visual alarm if ICG dye is present at a site within the ROI and pulsations at the site cease or fall below a threshold value. This can indicate that there was blood flow to the site when the ICG dye was injected, but the site has become occluded and trapped ICG dye may not be metabolized. In these and other embodiments, the method 1110 can highlight the site on the clinician display. In these and still other embodiments, the method 1110 can trigger different alarms for different events (e.g., the different combinations of information shown in the table 1450 in FIG. 14). For example, the method 1110 can trigger different alarms for the bottom three events illustrated in the table 1450. In these embodiments, the method 1110 can trigger a first audio and/or visual alarm when the method 1110 displays strong ICG information but weak or no RGB information, and a second audio and/or visual alarm (e.g., different than the first audio and/or visual alarm) when the method 1110 displays weak or no ICG information and weak or no RGB information. As a result, the method 1110 can alert a clinician that the site is at risk of hypoxia. In these and other embodiments, the method 1110 can trigger a third audio and/or visual alarm (e.g., an error alarm and/or an alarm different than the first and/or second alarms) when the method 1110 displays weak or no ICG information but strong RGB information. As a result, the method 1110 can alert a clinician that ICG information is missing (e.g., due to a lack of ICG dye at a site within the ROI).

In this manner, the enhanced ICG overlay can decrease the likelihood that a clinician determines there is blood flow to the site when ICG dye is present only because a decrease and/or cessation in blood flow has slowed metabolism of the ICG dye at the site. In turn, subsequent injections of ICG dye can provide a better indication of blood flow to and/or within a region. Thus, the video-based patient monitoring systems and associated methods disclosed herein have the potential to improve recordkeeping, improve patient care, reduce errors in vital sign measurements, increase frequency and accuracy of blood flow monitoring, help healthcare providers better characterize and respond to adverse medical conditions indicated by a decrease and/or cessation in blood flow, and generally improve monitoring of patients, along with many other potential advantages discussed below.

Although the steps of the method 1110 are discussed and illustrated in a particular order, the method 1110 in FIG. 11 is not so limited. In other embodiments, the method 1110 can be performed in a different order. In these and other embodiments, any of the steps of the method 1110 can be performed before, during, and/or after any of the other steps of the method 1110. Moreover, a person of ordinary skill in the relevant art will readily recognize that the illustrated method can be altered and still remain within these and other embodiments of the present technology. For example, one or more steps of the method 1110 illustrated in FIG. 11 can be omitted and/or repeated in some embodiments.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Furthermore, the various embodiments described herein may also be combined to provide further embodiments.

The systems and methods described here may be provided in the form of tangible and non-transitory machine-readable medium or media (such as a hard disk drive, hardware memory, etc.) having instructions recorded thereon for execution by a processor or computer. The set of instructions may include various commands that instruct the computer or processor to perform specific operations such as the methods and processes of the various embodiments described here. The set of instructions may be in the form of a software program or application. The computer storage media may include volatile and non-volatile media, and removable and non-removable media, for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic disk storage, or any other hardware medium which may be used to store desired information and that may be accessed by components of the system. Components of the system may communicate with each other via wired or wireless communication. The components may be separate from each other, or various combinations of components may be integrated together into a medical monitor or processor, or contained within a workstation with standard computer hardware (for example, processors, circuitry, logic circuits, memory, and the like). The system may include processing devices such as microprocessors, microcontrollers, integrated circuits, control units, storage media, and other hardware.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any material incorporated herein by reference conflicts with the present disclosure, the present disclosure controls. Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Furthermore, as used herein, the phrase "and/or" as in "A and/or B" refers to A alone, B alone, and both A and B. Additionally, the terms "comprising," "including," "having" and "with" are used throughout to mean including at least the recited feature(s) such that any greater number of the same feature and/or additional types of other features are not precluded.

From the foregoing, it will also be appreciated that various modifications may be made without deviating from the technology. For example, various components of the technology can be further divided into subcomponents, or that various components and functions of the technology may be combined and/or integrated. Furthermore, although advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:
1. A video-based patient monitoring system, comprising:
at least one processor; and
a non-contact detector having at least one video camera, wherein:
the at least one video camera is configured to:
capture a red, green, blue (RGB) video sequence of a region of interest (ROI) to generate an RGB view of the ROI; and
capture an indocyanine green (ICG) video sequence of the ROI to generate an ICG view of the ROI, and the at least one processor is configured to:
- calculate color changes in pixels of RGB images within the RGB video sequence;
- assign one or more colors from a predetermined color scheme to the pixels of the RGB images based at least in part on the sign and/or magnitude of the color changes to generate a pulsation field;
- calculate percentage ICG contours from the ICG video sequence; and
- superimpose the percentage ICG contours onto the pulsation field to generate an enhanced ICG overlay view.

2. The video-based patient monitoring system of claim 1, wherein the at least one video camera includes an RGB video camera, an infrared (IR) video camera, and/or a monochrome camera with a filter.

3. The video-based patient monitoring system of claim 1, wherein the enhanced ICG overlay view is a first enhanced ICG overlay view, and wherein the at least one processor is further configured to (i) superimpose the pulsation field onto the ICG view, (ii) blend the pulsation field with the ICG view to generate a second enhanced ICG overlay view, or (iii) both (i) and (ii).

4. The video-based patient monitoring system of claim 1, wherein the enhanced ICG overlay view is a first enhanced ICG overlay view, and wherein the at least one processor is further configured to calculate percentage pulsation contours from the RGB video sequence and to superimpose the percentage pulsation contours onto the ICG view to generate a second enhanced ICG overlay view.

5. The video-based patient monitoring system of claim 1, wherein the at least one processor is further configured to average magnitudes of the color changes to generate a pulsation strength field.

6. The video-based patient monitoring system of claim 5, wherein the ICG overlay view is a first enhanced ICG overlay view, and wherein the at least one processor is further configured to superimpose the pulsation strength field onto the ICG view to generate a second enhanced ICG overlay view.

7. The video-based patient monitoring system of claim 1, wherein the at least one video camera includes a filter, and/or wherein the video-based patient monitoring system further comprises a tuned IR light source configured to illuminate ICG dye within the ROI.

8. The video-based patient monitoring system of claim 1, further comprising a pulse oximeter, wherein the at least one processor is further configured to calculate a perfusion index using the pulse oximeter to calibrate the video-based patient monitoring system to the ROI.

9. A method for assessing blood flow within a region of interest (ROI), the method comprising:
- capturing a red, green, blue (RGB) video sequence of the ROI to generate an RGB view of the ROI, wherein the RGB video sequence of the ROI comprises at least two RGB images of the ROI;
- generating a pulsation field across the ROI to indicate blood flow within the ROI, the pulsation field being calculated from the RGB video sequence;
- capturing an indocyanine green (ICG) video sequence of the ROI to generate an ICG view of the ROI;
- generating percentage ICG contours, the percentage ICG contours being calculated from the ICG video sequence; and
- displaying the pulsation field and the percentage ICG contours together in an enhanced ICG overlay view.

10. The method of claim 9, wherein generating the pulsation field across the ROI includes computing changes in colors of pixels in the at least two RGB images across the RGB video sequence and assigning one or more colors from a predetermined color scheme to the pixels based at least in part on the sign and/or magnitude of the color changes to generate the pulsation field.

11. The method of claim 10, further comprising (i) replacing the colors of the pixels in the RGB video sequence with the assigned one or more colors from the predetermined color scheme to generate a pulsation field view of the ROI and (ii) displaying the pulsation field view.

12. The method of claim 9, wherein generating percentage ICG contours comprises iteratively applying one or more thresholds to the ICG view and extracting boundaries from the resulting non-zero regions.

13. The method of claim 12, wherein the one or more thresholds are predetermined, fixed, and/or relative to the range of ICG intensity values present and/or calculated in the ICG view.

14. The method of claim 9, wherein displaying the pulsation field and the percentage ICG contours together in the enhanced ICG overlay view comprises superimposing the RGB view including the pulsation field onto the ICG view including the percentage ICG contours.

15. The method of claim 9, wherein displaying the pulsation field and the percentage ICG contours together in the enhanced ICG overlay view comprises superimposing the ICG view including the percentage ICG contours onto the RGB view including the pulsation field.

* * * * *